(12) United States Patent
Glimcher et al.

(10) Patent No.: US 7,358,415 B2
(45) Date of Patent: Apr. 15, 2008

(54) METHODS AND COMPOSITIONS RELATING TO MODULATION OF HEPATOCYTE GROWTH, PLASMA CELL DIFFERENTIATION OR T CELL SUBSET ACTIVITY BY MODULATION OF XBP-1 ACTIVITY

(75) Inventors: Laurie H. Glimcher, West Newton, MA (US); Andreas M. Reimold, Dallas, TX (US)

(73) Assignee: President and Fellows of Harvard College, Cambridge, MA (US)

( * ) Notice: Subject to any disclaimer, the term of this patent is extended or adjusted under 35 U.S.C. 154(b) by 420 days.

(21) Appl. No.: 10/643,581

(22) Filed: Aug. 19, 2003

(65) Prior Publication Data

US 2004/0110236 A1   Jun. 10, 2004

Related U.S. Application Data

(62) Division of application No. 09/753,346, filed on Dec. 29, 2000, now Pat. No. 6,632,608.

(60) Provisional application No. 60/173,931, filed on Dec. 30, 1999.

(51) Int. Cl.
*G01N 33/00* (2006.01)
*C12Q 1/86* (2006.01)

(52) U.S. Cl. .............................. 800/3; 435/6; 435/7.1; 435/973

(58) Field of Classification Search ...................... None
See application file for complete search history.

(56) References Cited

U.S. PATENT DOCUMENTS

2004/0170622 A1 * 9/2004 Glimcher et al. ......... 424/130.1

FOREIGN PATENT DOCUMENTS

| EP | 0857780 A1 | 8/1998 |
|---|---|---|
| WO | WO-97/39721 A2 | 10/1997 |

OTHER PUBLICATIONS

Andersson, L-O. "Pharmacology of apolipoprotein A-I" *Curr. Opin. Lipidol.* 8:225-228 (1997).
Bancroft, A.J. et al. "Cytokine Production in BALB/c Mice Immunized with Radiation Attenuated Third Stage Larvae of the Filarial Nematode, Brugia pahangi" *J. Immunol.* 150(4):1395-1402 (Feb. 15, 1993).
Beg, A.A. et al. "Embryonic lethality and liver degeneration in mice lacking the RelA component of NF-κB" *Nature* 376:167-170 (Jul. 13, 1995).
Chen, B.P. et al. "Analysis of ATF3, a transcription factor induced by physiological stresses and modulated by gadd153/Chop10" *Mol. Cell Biol.* 16:1157-1168 (1996).
Chen, C. et al. "In Vitro Induction of T Cell Anergy by Blocking B7 and Early T Cell Costimulatory Molecule ETC-1/B7-2" *Immunity* 1:147-154 (May 1994).

Chen, H. et al. "Regulation and Activities of α-Fetoprotein" *Critical Reviews in Eukaryotic Gene Expression* 7(1&2):11-41 (1997).
Clauss, I.M. et al. "In Situ Hybridization Studies Suggest a Role for the Basic Region-Leucine Zipper Protein hXBP-1 in Exocrine Gland and Skeletal Development During Mouse Embryogenesis" *Dev. Dynamics* 197:146-156 (1993).
Clerici, M. et al. "A $T_H1 \rightarrow T_H2$ switch is a critical step in the etiology of HIV infection" *Immunol. Today* 14(3):107-111 (1993).
Dallman, M.J. "Cytokines and transplantation: Th1/Th2 regulation of the immune response to solid organ transplants in the adult" *Curr. Opin. Immunol.* 7:632-638 (1995).
Else, K.J. et al. "Cytokine-mediated Regulation of Chronic Intestinal Helminth Infection" *J. Exp. Med.* 179:347-351 (Jan. 1994).
Fässler, R. et al. "Consequences of lack of β1 integrin gene expression in mice" *Genes & Development* 9:1896-1908 (1995).
Fauci, A.S. "The Human Immunodeficiency Virus: Infectivity and Mechanisms of Pathogenesis" *Science* 239:617-623 (Feb. 5, 1988).
Fowler, D.H. et al. "Donor CD4-Enriched Cells of Th2 Cytokine Phenotype Regulate Graft-Versus-Host Disease Without Impairing Allogenic Engraftment in Sublethally Irradiated Mice" *Blood* 84(10):3540-3549 (Nov. 15, 1994).
Fowler, D.H. et al. "Donor Lymphoid Cells of Th2 Cytokine Phenotype Reduce Lethal Graft Versus Host Disease and Facilitate Fully Allogeneic Cell Transfers in Sublethally Irradiated Mice" Advances in Bone Marrow Purging and Processing: Fourth International Symposium. *Prog. Clin. Biol. Res.* 389:533-540 (1994).
Gabay, C. et al. "Acute-Phase Proteins and Other Systemic Responses to Inflammation" *New England Journal of Medicine* 340(6):448-454 (Feb. 11, 1999).
Gorczynski, R.M. et al. "Interleukin 12 in Combination With Anti-Interleukin 10 Reverses Graft Prolongation After Portal Venous Immunization" *Transplantation* 60(11):1337-1341 (Dec. 15, 1995).

(Continued)

*Primary Examiner*—Q. Janice Li
(74) *Attorney, Agent, or Firm*—Lahive & Cockfield LLP; Giulio A. DeConti, Jr.; Megan E Williams

(57) ABSTRACT

The invention demonstrates that the transcription factor XBP-1 is a regulator of hepatocyte growth, plasma cell differentiation and T cell subset activity. Methods for identifying modulators of hepatocyte growth, plasma cell differentiation and/or T cell subset activity, using XBP-1-containing indicator compositions or XBP-1-deficient cells, are provided. Methods of modulating hepatocyte growth, plasma cell differentiation and/or T cell subset activity (e.g., Th2 cytokine production) using agents that modulate the activity of XBP-1 are also provided. Methods for diagnosing disorders associated with aberrant hepatocyte growth, plasma cell differentiation and/or T cell subset activity, by assessing a change in XBP-1 expression, are also provided. XBP-1 deficient cells, animals and embryos, as well as kits for the methods of the invention, are also provided by the invention.

12 Claims, 6 Drawing Sheets

OTHER PUBLICATIONS

Grzych, J.-M. et al. "Egg Deposition is the Major Stimulus for the Production of Th2 Cytokines in Murine Schistosomiasis Mansoni" *J. Immunol.* 146(4):1322-1327 (Feb. 15, 1991).

Gualdi, R. et al. "Hepatic specification of the gut endoderm in vitro: cell signaling and transcription control" *Genes Dev.* 10:1670-1682 (1996).

Günes, C. et al. "Embryonic lethality and liver degeneration in mice lacking the metal-responsive transcriptional activator MTF-1" *EMBO J.* 17:2846-2854 (1998).

Hentsch, B. et al. "*Hlx* homeo box gene is essential for an inductive tissue interaction that drives expansion of embryonic liver and gut" *Genes Dev.* 10:70-79 (1996).

Hirsch, E. et al. "Impaired migration but not differentiation of haematopoietic stem cells in the absence of $\beta_1$ integrins" *Nature* 380:171-175 (Mar. 14, 1996).

Jacks, T. et al. "Effects of an *Rb* mutation in the mouse" *Nature* 359:295-300 (Sep. 24, 1992).

Khoury, S.J. et al. "Oral Tolerance to Myelin Basic Protein and Natural Recovery from Experimental Autoimmune Encephalomyelitis Are Associated with Downregulation of Inflammatory Cytokines and Differential Upregulation of Transforming Growth Factor β, Interleukin 4, and Prostaglandin E Expression in the Brain" *J. Exp. Med.* 176:1355-1364 (Nov. 1992).

Kishimoto, T. et al. "Enhanced Expression of a New Class of Liver-enriched b-Zip Transcription Factors, Hepatocarcinogenesis-related Transcription Factor, in Hepatocellular Carcinomas of Rats and Humans" *Cell Growth & Differentiation* 9:337-344 (Apr. 1998).

Kishimoto, T. et al. "HTF: A B-Zip Transcription Factor That Is Closely Related to the Human XBP/TREB5 and Is Activated by Hepatocellular Carcinoma in Rats" *Biochem. Biophys. Res. Commun.* 223:746-751 (1996).

Kullberg, M.C. et al. "Infection With *Schistosoma mansoni* Alters Th1/Th2 Cytokine Responses to a Non-Parasite Antigen" *J. Immunol.* 148(10):3264-3270 (May 15, 1992).

Lee, E. Y.-H. P. et al. "Mice deficient for Rb are nonviable and show defects in neurogenesis and haematopoiesis" *Nature* 359:288-294 (Sep. 24, 1992).

Levy, A.E. et al. "Administration of Ingraft Interleukin-4 Prolongs Cardiac Allograft Survival in Rats Treated With Donor-specific Transfusion/Cyclosporine" *Transplantation* 60:405-406 (Sep. 15, 1995).

Liou, H-C. et al. "A New Member of the Leucine Zipper Class of Proteins That Binds to the HLA DRα Promoter" *Science* 247:1581-1584 (Mar. 30, 1990).

Locksley, R.M. et al. "Helper T-cell subsets in mouse leishmaniasis: induction, expansion and effector function" *Immunoparasitology Today* 1:A58-A61 (1992).

Maeda, H. et al. "Adoptive transfer of a $T_h2$-like cell line prolongs MHC class II antigen disparate skin allograft survival in the mouse" *International Immunology* 6(6):855-862 (1994).

Maekawa. T. et al. "Mouse ATF-2 null mutants display features of a severe type of meconium aspiration syndrome" *J. Biol. Chem.* 274(25):17813-17819 (Jun. 18, 1999).

Mucenski, M.L. et al. "A Functional c-*myb* Gene Is Required for Normal Murine Fetal Hepatic Hematopoiesis" *Cell* 65:677-689 (May 17, 1991).

Ono, S.J. et al. "Human X-box binding protein 1 is required for the transcription of a subset of human class II major histocompatibility genes and forms a heterodimer with c-*fos*" *Proc. Natl. Acad. Sci. USA* 88:4309-4312 (May 1991).

Paul, W.E. et al. "Lymphocyte Responses and Cytokines" *Cell* 76:241-251 (Jan. 28, 1994).

Pearce, E.J. et al. "Downregulation of Th1 Cytokine Production Accompanies Induction of Th2 Responses by a Parasitic Helminth, *Schistosoma mansoni*" *J. Exp. Med.* 173:159-166 (Jan. 1991).

Pearlman, E. et al. "Induction of Murine T-Helper-Cell Responses to the Filarial Nematode *Brugia malayi*" *Infection and Immunity* 61(3):1105-1112 (Mar. 1993).

Pisa, P. et al. "Selective expression of interleukin 10, interferon γ, and granulocyte-macrophage colony-stimulating factor in ovarian cancer biopsies" *Proc. Natl. Acad. Sci. USA* 89:7708-7712 (Aug. 1992).

Rapoport. M.J. et al. "Interleukin 4 Reverses T Cell Proliferative Unresponsiveness and Prevents the Onset of diabetes in Nonobese Diabetic Mice" *J. Exp. Med.* 178:87-99 (Jul. 1993).

Reimold et al. "Transcription Factor B Cell Lineage-specific Activator Protein Regulates the Gene for Human X-Box Binding Protein 1" *J. Exp. Med.* 183:393-401 (Feb. 1996).

Reimold et al. "Chondrodysplasia and neurological abnormalities in ATF-2-deficient mice" *Nature* 379:262-265 (Jan. 18, 1996).

Reimold, A. et al. "Control of Terminal B Cell Differentiation by Transcription Factor XBP-1" *Arthritis & Rheumatism* 42(9 Suppl.):S58 (1999).

Reimold, A.M. et al. "An essential role in liver development for transcription factor XBP-1" *Genes & Development* 14:152-157 (2000).

Rudolph, D. et al. "Impaired fetal T cell development and perinatal lethality in mice lacking the cAMP response element binding protein" *Proc Natl Acad Sci U S A.* 95(8):4481-4486 (Apr. 14, 1998).

Schmidt, C. et al. "Scatter factor/hepatocyte growth factor is essential for liver development" *Nature* 373:699-702 (Feb. 23, 1995).

Servillo, G. et al. "Transcription factor CREM coordinates the timing of hepatocyte proliferation in the regenerating liver" *Genes Dev.* 12(23):3639-3643 (Dec. 1, 1998).

Shearer, G.M. et al. "T helper cell immune dysfunction in asymptomatic, HIV-1-seropositive individuals: the role of TH1-TH2 cross-regulation" *Chem. Immunol.* 54:21-43 (1992).

Simon, A.K. et al. "Divergent T-cell cytokine patterns in inflammatory arthritis" *Proc. Natl. Acad. Sci. USA* 91:8562-8566 (Aug. 1994).

Takeuchi, T. et al. "Heart Allografts in Murine Systems. The Differential Activation of TH2-Like Effector Cells in Peripheral Tolerance" *Transplantation* 53(6):1281-1291 (Jun. 1992).

Taub, R. "Transcriptional control of liver regeneration" *FASEB J.* 10:413-427 (1996).

Thai, N.L. et al. "Cytokine mRNA Profiles in Mouse Orthotopic Liver Transplantation" *Transplantation* 59(2):274-281 (Jan. 27, 1995).

Tzakis, A.G. et al. "Early Tolerance in Pediatric Liver Allograft Recipients" *J. Pediatr. Surg.* 29(6):754-756 (Jun. 1994).

Uehara, Y. et al. "Placental defect and embryonic lethality in mice lacking hepatocyte growth factor/scatter factor" *Nature* 373:702-705 (Feb. 23, 1995).

Yamamura, M. et al. "Local Expression of Antiinflammatory Cytokines in Cancer" *J. Clin. Invest.* 91:1005-1010 (Mar. 1993).

Yoshimura, T. et al. "Multiple cDNA clones encoding nuclear proteins that bind to the tax-dependent enhancer of HTLV-1: all contain a leucine zipper structure and basic amino acid domain" *EMBO J.* 9(8):2537-2542 (1990).

European Search Report for Application No. 05013817.1-2401, dated Mar. 17, 2006.

\* cited by examiner

US 7,358,415 B2

METHODS AND COMPOSITIONS RELATING TO MODULATION OF HEPATOCYTE GROWTH, PLASMA CELL DIFFERENTIATION OR T CELL SUBSET ACTIVITY BY MODULATION OF XBP-1 ACTIVITY

RELATED APPLICATIONS

This application is a divisional application of U.S. patent application Ser. No. 09/753,346, filed Dec. 29, 2000, now issued as U.S. Pat. No. 6,632,608, which claims the benefit of Provisional application 60/173,931 filed Dec. 30, 1999, the entire contents of which are incorporated herein by reference.

GOVERNMENT FUNDING

Work described herein was supported, at least in part, under grants AR43661 and A132412 awarded by the National Institutes of Health. The U.S. government therefore may have certain rights in this invention.

BACKGROUND OF THE INVENTION

Members of the CREB/ATF family of transcription factors form dimers and bind to cyclic-AMP response elements found in a large number of cellular promoters. The diversity of genes regulated by this large group of transcription factors is reflected in the essential functions of individual factors in fetal survival, neurological development, bone growth, and immune system activation (Rudolph et al. 1998, *Proc. Natl. Acad. Sci. USA*, 95:4481-4486; Reimold et al. 1996, *Nature*, 379:262-265; Maekawa et al. 1999, *J. Biol. Chem.* 274: 17813-17819). Recently, an important role in coordinating the timing of hepatocyte proliferation in the regenerating liver was demonstrated for the CREB/ATF family member CREM (Servillo et al 1998, *Genes Dev.* 12:3639-3643). In addition, the ATF-3 transcription factor was found to be induced in regenerating liver with the kinetics of an early response gene (Chen et al. 1996, *Mol. Cell. Biol.* 16:1157-1168).

The functions of a further CREB/ATF family member, XBP-1, have not been defined in detail. This transcription factor is expressed ubiquitously in adults but is mainly found in exocrine glands and bone precursors in the embryonic mouse (Liou et al. 1990, *Science* 247:1581-1584; Clauss et al. 1993, *Dev. Dynamics* 197:146-156). In vitro studies have demonstrated downregulation of the XBP-1 gene by BSAP, expression when antisense XBP-1 sequences are introduced into Raji cells (Reimold et al. 1996, *J. Exp. Med.*, 183:393-401; Ono et al. 1991, *Proc. Natl. Acad. Sci. USA* 88:4309-4312). Recently, the expression of XBP-1 was found to be dramatically increased in hepatocellular carcinomas (Kishimoto et al. 1998, *Cell Growth Diff.* 9:337-344), although whether this upregulation played a role in the malignant phenotype, or was merely a by-product of it, was not established.

SUMMARY OF THE INVENTION

This invention pertain to methods and compositions relating to modulation of hepatocyte growth, plasma cell differentiation and/or T cell subsets by modulation of XBP-1 activity. It has now been discovered that the transcription factor XBP-1 plays a critical role in regulating the growth of hepatocytes, the differentiation of plasma cells and the activity of T cell subsets. The invention is based, at least in part, on the observation that mice lacking XBP-1 have severely impaired hepatocyte development, identifying XBP-1 as a transcription factor essential for hepatocyte growth and, furthermore, that mice lacking XBP-1 are severely impaired in plasma cell generation and exhibit defects in production of Th2 cytokines, identifying XBP-1 as a transcription factor essential for plasma cell differentiation and involved in regulation of T cell subsets. To our knowledge this is the first demonstration of a role for XBP-1 in regulating hepatocyte growth, plasma cell differentiation and T cell subsets.

The invention provides methods for identifying compounds that modulate hepatocyte growth, plasma cell differentiation and/or T cell subsets, methods for modulating hepatocyte growth, plasma cell differentiation and/or T cell subsets using agents that modulate XBP-1 activity (e.g., methods to expand hepatocytes in culture by stimulating XBP-1 activity in the cells such that proliferation of the hepatocytes is stimulated, methods for differentiating plasma cells in culture by stimulating XBP-1 activity in the cells such that differentiation of the plasma cells is stimulated and/or methods for modulating Th2 cytokine production by modulating XBP-1 activity) and methods for diagnosing disorders associated with aberrant hepatocyte growth, plasma cell differentiation and/or T cell subset activity based on assessing a change in the expression of XBP-1 (e.g., the level of expression or the form of XBP-1 expressed), hi one aspect, the invention pertains to methods for identifying compounds that modulate hepatocyte growth, plasma cell differentiation and/or T cell subset activity. In one embodiment, the invention provides a method for identifying a compound that modulates hepatocyte growth, plasma cell differentiation and/or T cell subset activity using an indicator composition comprising XBP-1 protein, wherein a test compound that modulates the activity of XBP-1 is selected and then the effect of this selected compound on hepatocyte growth, plasma cell differentiation or T cell subset activity (e.g., Th2 cytokine production) is assessed, hi the method, the indicator composition comprising XBP-1 first is contacted with each member of a library of test compounds. The test compound(s) that modulate the activity of XBP-1 protein are selected and the ability of the selected compound(s) to modulate hepatocyte growth, plasma cell differentiation and/or T cell subset activity (e.g., Th2 cytokine production) is determined. The indicator composition can be, for example, a cell that expresses XBP-1 protein, a cell that has been engineered to express the XBP-1 protein by introducing an expression vector encoding the XBP-1 protein into the cell or a cell free corhpositioa Alternatively, the indicator composition may be a cell or cell-free composition that includes an XBP-1 protein and a target molecule, and the ability of the test compound to modulate the interaction of the XBP-1 protein with a target molecule is monitored. In another embodiment, the indicator composition is an indicator cell, which comprises an XBP-1 protein and a reporter gene responsive to the XBP-1 proteia The level of expression of the reporter gene can be used to determine the ability of a test compound to modulate the activity of XBP-1 protein by producing an indicator cell that contains a recombinant expression vector encoding the XBP-1 protein and a vector comprising an XBP-1-responsive regulatory element operatively linked a reporter gene. The indicator cell is contacted with a test compound and the level of expression of the reporter gene in the indicator cell in the presence of the test compound is determined. By comparing the level of expression of the reporter gene in the indicator cell in the presence of the test compound with the level of expression of the reporter gene in the indicator cell in the absence of the test compound, a compound of interest that modulates the activity of XBP-1 protein can be determined.

In another embodiment of the method for identifying compounds that modulate hepatocyte growth or plasma cell differentiation, a test compound(s) is contacted with a hepatocyte or a plasma cell precursor (B cell) or a T cell deficient in XBP-1 and the effect of the test compound(s) on growth, differentiation and/or activity of the cell is determined, to thereby identify compounds that modulate hepatocyte growth, plasma cell differentiation and/or T cell subset activity via means other than through XBP-1 (i.e., compounds that can "rescue" the XBP-1-deficient phenotype). For example, a compound that induces growth of XBP-1 deficient hepatocytes or that induces differentiation of XBP-1 deficient B cells into plasma cells or that induces production of a Th2 cytokine(s) by XBP-1 deficient T cells can be selected.

In another aspect, the invention pertains to a method for modulating hepatocyte growth, plasma cell differentiation and/or T cell subset activity by contacting hepatocytes, hepatocyte precursors, plasma cells, plasma cell precursors (B cells), T cells or T cell precursors with a modulator of XBP-1 activity such that the growth of the hepatocytes, differentiation of the plasma cells and/or activity of T cell subsets is modulated. In one aspect, this modulatory method pertains to methods of expanding hepatocytes or plasma cells in vitro, through culture of the cells with a stimulator of XBP-1 activity such that growth of the hepatocytes or differentiation of the plasma cells is stimulated These in vitro methods allow for the expansion of hepatocytes for use in the treatment of, for example, hepatic injury, hepatic failure due to disease (e.g., viral infections, such as hepatitis) or hepatic failure due to toxins (e.g., cirrhosis of the liver). These in vitro methods also allow for the expansion of plasma cells for use in the treatment of, for example, immunodeficiencies characterized by decreased antibody production, as well for general stimulation of humoral immune responses to pathogens. Furthermore, these in vitro methods allow for modulation of production of Th2 cytokines.

In another aspect, this modulatory method pertains to methods of modulating aberrant hepatocyte growth, plasma cell differentiation and/or T cell subset activity in a subject by administering to the subject a therapeutically effective amount of a specific modulator of XBP-1 activity such that aberrant hepatocyte growth, plasma cell differentiation and/ or T cell subset activity in a subject is modulated. In one embodiment, the modulator inhibits XBP-1 activity, for example, an antisense oligonucleotide, an intracellular antibody or a peptide that inhibits the interaction of XBP-1 with another protein, such that hepatocyte growth or plasma cell differentiation in the subject is inhibited, or production of Th2 cytokines is inhibited. Such inhibitory methods may be useful in, for example, hepatocellular carcinoma, multiple myeloma, autoimmune disorders associated with the production of pathogenic autoantibodies (e.g., systemic lupus erythematosus), and disorders associated with excess Th2 cell activity. hi another embodiment, the modulator stimulates XBP-1 activity, for example, an expression vector encoding XBP-1, such that hepatocyte growth or plasma cell differentiation is stimulated, or Th2 cytokine production is stimulated, in the subject. Such stimulatory methods may be useful in the treatment of, for example, hepatic injury, hepatic failure due to hepatic disease, hepatic failure due to hepatic toxins, immunodeficiency disorders characterized by decreased antibody production, or disorders associated with deficient Th2 cell activity. Stimulation of plasma cell differentiation also may be useful in, for example, stimulation of humoral responses to pathogens and in increasing the efficiency of vaccinations. In the aforementioned modulatory methods, the modulator can be administered directly to, for example, the liver of a subject, a site of plasma cell differentiation in the subject or a site of T cell subset activity. Alternatively, the modulator can be contacted ex vivo with hepatocytes, hepatocyte precursors, plasma cells, plasma cell precursors, T cells or T cell precursors isolated from a subject, followed by administration of the cells back into the subject.

In another aspect, the invention pertains to a method of diagnosing a subject for a disorder associated with aberrant hepatocyte growth, plasma cell differentiation and/or T cell subset activity by detecting a change in expression of XBP-1 in cells of a subject suspected of having a disorder associated with aberrant hepatocyte growth, plasma cell differentiation and/or T cell subset activity. The expression of XBP-1 in cells of a subject suspected of having the disorder is compared, for example, to the expression of XBP-1 in cells of a control subject without the disorder. The diagnosis for a disorder in a subject is based on a change in expression of XBP-1 (e.g., the level or form of XBP-1) in cells relative to a control subject. Elevated levels of XBP-1 expression, or expression of a more active form of XBP-1 (e.g., a constitutively active mutant form of XBP-1) may be associated with a disorder characterized by increased hepatocyte growth (e.g., hepatocellular carcinoma), plasma cell differentiation (e.g., multiple myeloma or autoimmune diseases characterized by production of pathogenic autoantibodies, such as systemic lupus; erythematosus) or Th2 cell activity (e.g., allergy, cancer, infectious diseases) while reduced levels of XBP-1 expression or expression of an inactive mutant form of XBP-1 may be associated with a disorder characterized by decreased hepatocyte growth, plasma cell differentiation (e.g., immunodeficiency disorders), or Th2 cell activity (e.g. certain autoimmune diseases).

XBP-1 deficient cells and non-human animals (e.g. mice) for use in the screening methods of the invention are also provided. XBP-1 deficient cells, such as hepatocytes, can be obtained from early embryos of XBP-1 deficient animals (prior to lethality in utero). Furthermore, blastocyst complementation can be used to create animals deficient both in XBP-1 and a second gene (e.g., RAG-2), to obtain viable animals in which XBP-1 deficient cells contribute to certain cell compartments, such as the lymphoid system to thereby obtain XBP-1 deficient B cells and T cells. Still further, the invention provides animals having a homozygous disruption in the endogenous XBP-1 gene but that carry an XBP-1 transgene driven by a liver -specific promoter (such as the albumin promoter).

Kits for performing the various methods of the invention are also encompassed by the invention.

DETAILED DESCRIPTION OF THE INVENTION

Figure 1:
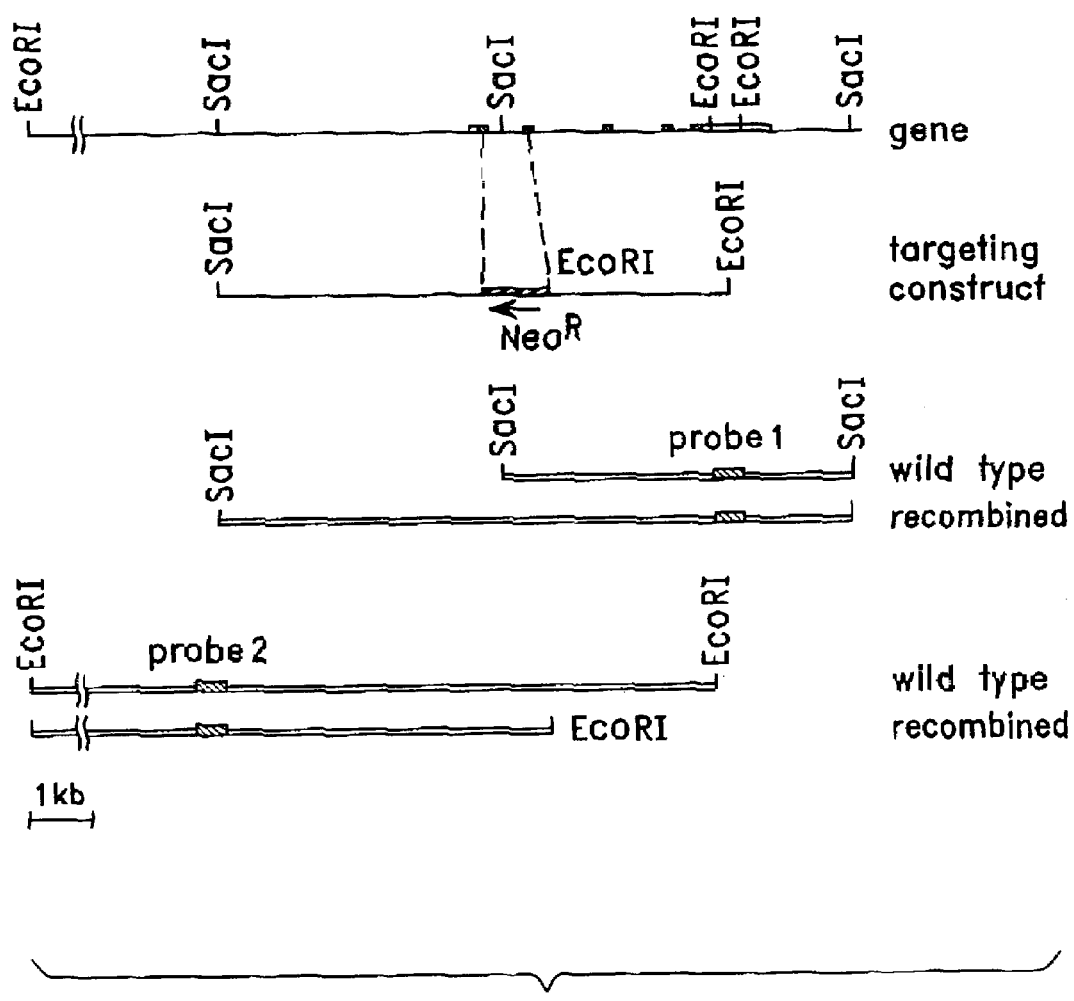
FIG. 1 is a schematic diagram of the construct used to disrupt the XBP-1 gene in mice. Parts of XBP-1 exons 1 and 2 were deleted and replaced by the neo resistance gene, in the opposite orientation from XBP-1.

This invention pertains to methods and compositions relating to modulation of hepatocyte growth, plasma cell differentiation and/or T cell subset activity by modulation of XBP-1 activity. The invention is based, at least in part, on the discovery that mice deficient for the XBP-1 protein exhibit strikingly hypoplastic fetal livers due to severely impaired hepatocyte development. This impaired development was the result of both diminished growth rate and prominent apoptosis. Specific target genes of XBP-1 in the liver were identified as acute phase protein family members, including a-1 antitrypsin and a-fetoprotein (AFP). Thus, the data described herein identify XBP-1 as a transcription factor essential for hepatocyte growth. Since XBP-1 deficient mice die in utero from hypoplastic livers, RAG-2-deficient blastocyst complementation was used to examine the role of XBP-1 in the lymphoid system. It further was discovered that chimeric mice made using this complementation system secrete very little serum immunoglobulin of any isotype secondary to failure to generate the plasma cell compartment Accordingly, the invention is also based, at least in part, on the discovery that XBP-1 is a transcription factor that has now been demonstrated to be required for generation of plasma cells. Still further, it was discovered that T cells from XBP-1 deficient mice display a defect in their ability to secrete cytokines of the Th2 type (e.g., IL-4, IL-10, IL-5, IL-6). Accordingly, the invention is also based, at least in part, on the discovery that XBP-1 is a transcription factor that has now been demonstrated to be involved in regulating Th2 cytokine production and thus in regulating the activity of T cell subsets (i.e., Th1 vs. Th2 activity).

In one aspect, the invention pertains to a method of identifying a compound that modulates hepatocyte growth, plasma cell differentiation and/or T cell subset activity. In one embodiment of these screening assays, an indicator composition that includes XBP-1 is used to identify and select compounds that modulate XBP-1 activity and then the effect of the selected compounds on hepatocyte growth, plasma cell differentiation or Th2 cytokine production is evaluated. In another embodiment of these screening assays, hepatocytes, B cells or T cells deficient in XBP-1 are contacted with a test compound and the effect of the compound on hepatocyte growth, plasma cell differentiation or T cell subset activity is determined to identify compounds that modulate hepatocyte growth, plasma cell differentiation or T cell subset activity through "rescue" of the XBP-1 deficient phenotype.

In another aspect, the invention pertains to method for modulating growth of hepatocytes, differentiation of plasma cells or T cell subset activity, either in vitro or in vivo, using modulators of XBP-1 activity. In one embodiment, hepatocytes, hepatocyte precursors, plasma cells, plasma cell precursors (B cells) or T cells (e.g., isolated from a subject) are contacted with a stimulatory modulator compound by culturing the cells with the modulator in vitro, to thereby stimulate hepatocyte growth, plasma cell differentiation or Th2 cytokine production. The hepatocytes that grow out in culture or plasma cells that have formed upon differentiation of B cells in culture or Th2 type cells that differentiate in culture, can then be readministered to the subject In another embodiment, aberrant hepatocyte growth, plasma cell differentiation or T cell subset activity in a subject is modulated by administering to the subject a therapeutically effective amount of an inhibitory modulator of XBP-1 activity such that aberrant hepatocyte growth, plasma cell differentiation or T cell subset activity in a subject is modulated. Use of modulators that inhibit or stimulate XBP-1 activity are encompassed by the modulatory methods of the invention.

In yet another aspect, the invention pertains to a method of diagnosing a subject for a disorder associated with aberrant hepatocyte growth, plasma cell differentiation or T cell subset activity by detecting a change in expression of XBP-1 in hepatocytes (or hepatocyte precursors) or plasma cells (or plasma cell precursors) or T cells (or T cell precursors) of a subject suspected of having a disorder associated with aberrant hepatocyte growth or plasma cell differentiation or T helper cell differentiation.

So that the invention may be more readily understood, certain terms are first defined, As used herein, the term "XBP-1 is intended to refer to a human protein that is a DNA binding protein and has an amino acid sequence as described in, for example, Liou, H-C. et al. (1990) *Science* 247:1581-1584 and Yoshimura, T. et al. (1990) *EMBO J.* 9:2537-2542, and other mammalian homologs thereof, such as described in Kishimoto T. et al, (1996) *Biochem. Biophys. Res. Commun.* 223:746-751 (rat homologue). Proteins intended to be encompassed by the term "XBP-1" include those having amino acid sequences disclosed in GenBank with accession numbers A36299, 4827058, P17861, CAA39149 and BAA82600. XBP-1 is also referred to in the art as and TREB5 or HTF.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (i.e., contacting a cell e.g., a cell, with an compound) is intended to include incubating the compound and the cell together in vitro (e.g., adding the compound to cells in culture) and administering the compound to a subject such that the compound and cells of the subject are contacted in vivo. The term "contacting" is not intended to include exposure of cells to a XBP-1 modulator that -may occur naturally in a subject (i.e., exposure that may occur as a result of a natural physiological process).

As used herein, the term "test compound" is intended to refer to a compound that has not previously been identified as, or recognized to be, a modulator of XBP-1 activity and/or of hepatocyte growth and/or plasma cell differentiation and/or T cell subset activity.

The term "library of test compounds" is intended to refer to a panel comprising a multiplicity of test compounds.

As used herein, the term "cells deficient in XBP-1" is intended to include cells of a subject that are naturally deficient in XBP-1, as wells as cells of a non-human XBP-1 deficient animal, e.g., a mouse, that have been altered such that they are deficient in XBP-1. The term "cells deficient in XBP-1 is also intended to include cells isolated from a non-human XBP-1 deficient animal or a subject that are cultured in vitro.

As used herein, the term "non-human XBP-1 deficient animal" refers to a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal, such that the endogenous XBP-1 gene is altered, thereby leading to either no production of XBP-1 or production of a mutant form of XBP-1 having deficient XBP-1 activity. Preferably, the activity of XBP-1 is entirely blocked, although partial inhibition of XBP-1 activity in the animal is also encompassed. The term "non-human XBP-1 deficient animal" is also intended to encompass chimeric animals (e.g., mice) produced using a blastocyst complementation system, such as the RAG-2 blastocyst complementation system, in which a particular organ or organs (e.g., the lymphoid organs) arise from embryonic stem (ES) cells with homozygous mutations of the XBP-1 gene.

As used herein, the term "indicator composition" refers to a composition that includes XBP-1 protein, for example, a cell that naturally expresses XBP-1 protein, a cell that has been engineered to express the XBP-1 protein by introducing an expression vector encoding the XBP-1 protein into the cell, or a cell free composition that contains XBP-1 (e.g., naturally-occurring XBP-1 or recombinantly-engineered XBP-1).

As used herein, the term "engineered" (as in an engineered cell) refers to a cell into which an expression vector encoding the XBP-1 protein has been introduced.

As used herein, the term "cell free composition" refers to an isolated composition, which does not contain intact cells. Examples of cell free compositions include cell extracts and compositions containing isolated proteins.

As used herein, the term "a target molecule" for XBP-1 refers a molecule with which XBP-1 can interact, including other proteins and DNA sequences, including for example, the promoter/enhancer regions of genes such as a-1 antitrypsin, a-fetoprotein, HLA DRo, and the 21 base pair repeat enhancer of HTLV-1 LTR, and other b-ZIP proteins such as c-Fos.

As used herein, the term "reporter gene responsive to XBP-1" refers to any gene that expresses a detectable gene product, which may be RNA or protein. Preferred reporter genes are those that are readily detectable. The reporter gene may also be included in a construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), *Nature* 282: 864-869) luciferase, and other enzyme detection systems, such as beta-galactosidase; firefly luciferase (deWet et al. (1987), *Mol. Cell. Biol.* 7:725-737); bacterial luciferase (Engebrecht and Silverman (1984), *PNAS* 1:4154-4158; Baldwin et al. (1984), *Biochemistry* 23: 3663-3667); alkaline phosphatase (Toh et al. (1989) *Eur. J. Biochem.* 182: 231-239, Hall et al. (1983)/. *Mol. Appl. Gen.* 2: 101), human placental secreted alkaline phosphatase (Cullen and Malim (1992) *Methods in Enzymol.* 216:362-368) and green fluorescent protein (U.S. Pat. No. 5,491,084; WO 96/23898).

As used herein, the term "XBP-1-responsive element" refers to a DNA sequence that is directly or indirectly regulated by the activity of the XBP-1 (whereby activity of XBP-1 can be monitored, for example, via transcription of the reporter genes).

As used herein, the term "aberrant" (as in aberrant hepatocyte growth or plasma cell differentiation) refers to growth or differentiation that deviates from normal growth or differentiation in a subject. The aberrant growth or differentiation can either be excessive growth or differentiation or reduced growth or differentiation with respect to normal growth or differentiation in a subject.

As used herein, the term "a modulator of XBP-1 activity" is intended to refer to an agent, for example a compound or compounds, which modulates transcription of an XBP-1 gene, translation of XBP-1 mRNA or activity of an XBP-1 protein. A "modulator of XBP-1 activity" also includes compounds that indirectly modulate XBP-1 activity, for example, modulators of a signal transduction pathway that may include XBP-1. Examples of modulators that directly modulate XBP-1 activity include antisense nucleic acid molecules that bind to XBP-1 mRNA or genomic DNA, intracellular antibodies that bind to XBP-1 intracellularly and modulate (i.e., inhibit) XBP-1 activity, XBP-1 peptides that inhibit the interaction of XBP-1 with a target molecule (e.g., c-Fos) and expression vectors encoding XBP-1 that allow for increased expression of XBP-1 activity in a cell, as well as chemical compounds that act to specifically modulate the activity of XBP-1.

As used herein, an "antisense oligonucleotide" refers to a nucleic acid that comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

As used herein, the term "intracellular antibody" is intended to include immunoglobulin molecules and immunologically active portions of immunoglobulin molecules, i.e., molecules that contain an antigen binding site which specifically binds (immunoreacts with) an antigen, such as Fab and F(ab')2 fragments. The term "intracellular antibody" is also intended to refer to an antibody that functions in an intracellular region of a cell, e.g., the cytoplasm or nucleus, to modulate the expression or activity of the XBP-1.

As used herein, the term "diagnosing" refers to identifying a disorder in a subject or the susceptibility of a subject to the disorder (e.g., a predisposition to develop a disorder).

As used herein, the term "T cell subset activity" refers to the activity of Th1 versus Th2 helper T cells. T cell subset activity can be modulated by upregulating Th2 cell activity, downregulating Th2 cell activity, upregulating Th1 cell activity or downregulating Th1 cell activity.

As used herein, the term "Th2 cytokine" refers to cytokines produced predominantly by Th2 cells (rather than Th1 cells) and include (but are not limited to) IL-4, IL-10, IL-5 and IL-6.

Various aspects of the present invention are described in further detail in the following subsections.

I. Screening Assays to Identify Compounds that Modulate Hepatocyte Growth and/or Plasma Cell Differentiation and/or T Cell Subset Activity A. Assays Using XBP-1-Containing Indicator Compositions In one embodiment, the invention provides methods for identifying compounds that modulate hepatocyte growth or plasma cell differentiation or T cell subset activity using indicator compositions that include XBP-1. As described in the Examples, XBP-1 has been demonstrated to be a regulator of hepatocyte growth, plasma cell differentiation and T cell subset activity. Accordingly, compounds that specifically modulate the activity of XBP-1 can be identified, as described herein, and the effect of a selected test compound on hepatocyte growth or plasma cell differentiation or T cell subset activity can be evaluated.

Thus, another aspect of the invention pertains to screening assays for identifying compounds that modulate hepatocyte growth or plasma cell differentiation or T cell subset activity comprising, providing an indicator composition comprising XBP-1 protein;

contacting the indicator composition with each member of a library of test compounds;

selecting from the library of test compounds a compound of interest that modulates the activity of XBP-1 protein; and determining the effect of the compound of interest on hepatocyte growth or plasma cell differentiation or T cell subset activity (e.g., Th2 cytokine production) to thereby identify a compound that modulates hepatocyte growth or plasma cell differentiation or T cell subset activity.

The indicator composition can be a cell that expresses XBP-1 protein, for example, a cell that naturally expresses XBP-1 or, more preferably, a cell that has been engineered to express the XBP-1 protein by introducing into the cell an expression vector encoding the XBP-1 protein. Alternatively, the indicator composition can be a cell-free composition that includes XBP-1 (e.g., a cell extract from an XBP-1-expressing cell or a composition that includes purified XBP-1 protein, either natural XBP-1 or recombinant XBP-1). In one embodiment, the indicator composition includes an XBP-1 protein and a target molecule with which XBP-1 interacts, and the ability of the test compound to modulate the interaction of the XBP-1 protein with a target molecule is monitored to thereby identify the test compound as a modulator of XBP-1 activity.

In preferred embodiments, the indicator composition comprises an indicator cell, wherein the indicator cell comprises an XBP-1 protein and a reporter gene responsive to the XBP-1.protein. Preferably, the indicator cell contains:

a recombinant expression vector encoding the XBP-1 protein; and a vector comprising an XBP-1-responsive regulatory element operatively linked a reporter gene; and the screening method comprises:

contacting the indicator cell with a test compound;

determining the level of expression of the reporter gene in the indicator cell in the presence of the test compound; and comparing the level of expression of the reporter gene in the indicator cell in the presence of the test compound with the level of expression of the reporter gene in the indicator cell in the absence of the test compound to thereby select a compound of interest that modulates the activity of XBP-1 protein.

Once a test compound is identified as modulating the activity of XBP-1, the effect of the test compound on hepatocyte growth or plasma cell differentiation or T cell subset activity is then tested.

XBP-1-responsive elements that can be used in the reporter gene construct are known in the art and include, for example, upstream regulatory regions from genes such as a-1 antitrypsin, a-fetoprotein, HLA DRo, as well as the 21 base pair repeat enhancer of the HTLV-1LTR. An examples of an XBP-1-responsive reporter gene is the HLA DRa-CAT construct described in Ono, S. J. et al. (1991) *Proc. Natl. Acad. Sci. USA* 88:4309-4312.

A cell that has been engineered to express the XBP-1 protein can be produced by introducing into the cell an expression vector encoding the XBP-1 protein. Recombinant expression vectors that can be used for expression of XBP-1 protein in the indicator cell are known in the. art. Typically the XBP-1 cDNA is first introduced into a recombinant expression vector using standard molecular biology techniques. An XBP-1 cDNA can be obtained, for example, by amplification using the polymerase chain reaction (PCR) or by screening an appropriate cDNA library. The nucleotide sequences of XBP-1 cDNAs (e.g., human and rat) are known in the art and can be used for the design of PCR primers that allow for amplification of a cDNA by standard PCR methods or for the design of a hybridization probe that can be used to screen a cDNA library using standard hybridization methods. The nucleotide and predicted amino acid sequences of a mammalian XBP-1 cDNA are disclosed in Liou, H-C. et al. (1990) *Science* 247:1581-1584, Yoshimura, T. et al. (1990) *EMBO J.* 9:2537-2542, and Kishimoto T. et al., (1996) *Biochem. Biophys. Res. Commun.* 223:746-751.

Following isolation or amplification of a XBP-1 cDNA, the DNA fragment is introduced into an expression vector. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility hi recombinant DNA techniques are often in the form of plasmids. hi the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid in a form suitable for expression of the nucleic acid in a host cell, which means that the recombinant expression vectors include one or more regulatory sequences, selected on the basis of the host cells to be used for expression and the level of expression desired, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell, those which direct expression of the nucleotide sequence only in certain host cells (e.g., tissue-specific regulatory sequences) or those which direct expression of the nucleotide sequence only under certain conditions (e.g., inducible regulatory sequences).

It will be appreciated by those skilled in the art that the design of the expression vector may depend on such factors as the choice of the host cell to be transformed, the level of expression of protein desired, etc. When used in mammalian cells, the expression vector's control functions are often provided by viral regulatory elements. For example, commonly used promoters are derived from polyoma virus, adenovirus, cytomegalovirus and Simian Virus 40. Non-limiting examples of mammalian expression vectors include pCDMS (Seed, B., (1987) *Nature* 329:840) and pMT2PC (Kaufman et al. (1987), *EMBO J.* 6:187-195). A variety of mammalian expression vectors carrying different regulatory sequences are commercially available. For constitutive expression of the nucleic acid in a mammalian host cell, a preferred regulatory element is the cytomegalovirus promoter/enhancer. Moreover, inducible regulatory systems for use in mammalian cells are known in the art, for example systems in which gene expression is regulated by heavy metal ions (see e.g., Mayo et al. (1982) *Cell* 29:99-108; Brinster et al. (1982) *Nature* 296:39-42; Searle et al. (1985) *Mol Cell. Biol.* 5:1480-1489), heat shock (see e.g., Nouer et al. (1991) in *Heat Shock Response*, e.d. Nouer, L., CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al. (1987) *Nature* 329:734-736; Israel & Kaufman (1989) *Nucl. Acids Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313). Still further, many tissue-specific regulatory sequences are known in the art, including the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916) and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:3 74-3 79) and the a-fetoprotein promoter (Campes and Tilghman (1989) *Genes Dev.* 3:537-546).

Vector DNA can be introduced into mammalian cells via conventional transfection techniques. As used herein, the various forms of the term "transfection" are intended to refer to a variety of art-recognized techniques for introducing foreign nucleic acid (e.g., DNA) into mammalian host cells, including calcium phosphate co-precipitation, DEAE-dextran-mediated transfection, lipofection, or electroporation. Suitable methods for transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on a separate vector from that encoding XBP-1 or, more preferably, on the same vector. Cells stably transfected with the introduced nucleic acid can be identified by drug selection (e.g., cells that have incorporated the selectable marker gene will survive, while the other cells die).

In another embodiments, the indicator composition is a cell free composition. XBP-1 expressed by recombinant methods in a host cells or culture medium can be isolated from the host cells, or cell culture medium using standard methods for protein purifying, for example, by ion-exchange chromatography, gel filtration chromatography, ultrafiltration, electrophoresis, and immunoaffinity purification with antibodies specific for XBP-1 to produce XBP-1 protein that can be used in a cell free composition. Alternatively, an extract of XBP-1-expressing cells can be prepared for use as cell-free composition.

In one embodiment, compounds that specifically modulate XBP-1 activity are identified based on their ability to modulate the interaction of XBP-1 with a target molecule to which XBP-1 binds. The target molecule can be a protein, such as c-Fos. Alternatively, the target can be a DNA sequence (i.e., an XBP-1-responsive element). Suitable assays are known in the art that allow for the detection of protein-protein interactions (e.g., immunoprecipitations, two-hybrid assays and the like) or that allow for the detection of interactions between a DNA binding protein with a target DNA sequence (e.g., electrophoretic mobility shift assays, DNase I footprinting assays and the like). By performing such assays in the presence and absence of test compounds, these assays can be used to identify compounds that modulate (e.g., inhibit or enhance) the interaction of XBP-1 with a target molecule.

In one embodiment, the amount of binding of XBP-1 to the target molecule in the presence of the test compound is greater than the amount of binding of the XBP-1 to the target molecule in the absence of the test compound, in which case the test compound is identified as a compound that enhances binding of XBP-1. In another embodiment, the amount of binding of the XBP-1 to the target molecule in the presence of the test compound is less than the amount of binding of the XBP-1 to the target molecule in the absence of the test compound, in which case the test compound is identified as a compound that inhibits binding of XBP-1.

In the methods of the invention for identifying test compounds that modulate an interaction between XBP-1 protein and a target molecule, the full XBP-1 protein may be used in the method, or, alternatively, only portions of the XBP1 protein may be used. For example, an isolated XBP-1b-ZIP structure (or a larger subregion of XBP-1 that includes the b-ZIP structure) can be used. The degree of interaction between XBP-1 proteins and the target molecule can be determined, for example, by labeling one of the proteins with a detectable substance (e.g., a radiolabel), isolating the non-labeled protein and quantitating the amount of detectable substance that has become associated with the non-labeled protein. The assay can be used to identify test compounds that either stimulate or inhibit the interaction between the XBP-1 protein and a target molecule. A test compound that stimulates the interaction between the XBP-1 protein and a target molecule is identified based upon its ability to increase the degree of interaction between the XBP-1 protein and a target molecule as compared to the degree of interaction in the absence of the test compound, whereas a test compound that inhibits the interaction between the XBP-1 protein and a target molecule is identified based upon its ability to decrease the degree of interaction between the XBP-1 protein and a target molecule as compared to the degree of interaction in the absence of the compound.

Recombinant expression vectors that can be used for expression of XBP-1 in the indicator cell are known in the art (see discussions above). In one embodiment, within the expression vector the XBP-1-coding sequences are operatively linked to regulatory sequences that allow for constitutive expression of XBP-1 in the indicator cell (e.g., viral regulatory sequences, such as a cytomegalovirus promoter/enhancer, can be used). Use of a recombinant expression vector that allows for constitutive expression of XBP-1 in the indicator cell is preferred for identification of compounds that enhance or inhibit the activity of XBP-1. In an alternative embodiment, within the expression vector the XBP-1 coding sequences are operatively linked to regulatory sequences of the endogenous XBP-1 gene (i.e., the promoter regulatory region derived from the endogenous gene). Use of a recombinant expression vector in which XBP-1 expression is controlled by the endogenous regulatory sequences is preferred for identification of compounds that enhance or inhibit the transcriptional expression of XBP-1.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

A variety of cell types are suitable for use as an indicator cell in the screening assay. Preferably a cell line is used which expresses low levels of endogenous XBP-1, which is then engineered to express recombinant XBP-1.

hi one embodiment, the level of expression of the reporter gene in the indicator cell in the presence of the test compound is higher than the level of expression of the reporter gene in the indicator cell in the absence of the test compound and the test compound is identified as a compound that stimulates the expression or activity of XBP-1. In another embodiment, the level of expression of the reporter gene in the indicator cell in the presence of the test compound is lower than the level of expression of the reporter gene in the indicator cell in the absence of the test compound and the test compound is identified as a compound that inhibits the expression or activity of XBP-1.

Alternative to the use of a reporter gene construct, compounds that modulate the expression or activity of XBP-1 can be identified by using other "read-outs." For example, an indicator cell can be transfected with an XBP-1 expression vector, incubated in the presence and in the absence of a test compound, and proliferation and/or differentiation the cells, can be used as an indicator of XBP-1 modulation. Cell proliferation/differentiation can be monitored directly (e.g., cell counts or radiolabeled thymidine uptake, for monitoring cell proliferation, or microscopic examination of the cells for monitoring cell differentiation), or indirectly by monitoring one or more markers of cell proliferation or differentiation (e.g., an increase in mRNA for a gene produce associated with cell proliferation or differentiation, or the secretion of a gene product associated with cell proliferation or differentiation, such as the secretion of immunoglobulin by differentiated plasma cells or the secretion of Th2 cytokines by differentiated Th2 cells). Standard methods for detecting mRNA of interest, such as reverse transcription-polymerase chain reaction (RT-PCR) and Northern blotting, are known in the art. Standard methods for detecting protein secretion in culture supematants, such as enzyme linked immunosorbent assays (ELISA), are also known in the art.

Once a test compound is identified that modulates XBP-1 activity, by one of the variety of methods described hereinbefore, the selected test compound (or "compound of interest") can then be further evaluated for its effect on hepatocyte growth or plasma cell differentiation or T cell subset activity, for example by contacting the compound of interest with hepatocyte or B cells or T cells either in vivo (e.g., by administering the compound of interest to a subject) or ex vivo (e.g., by isolating hepatocytes or B cells or T cells and contacting the isolated cells with the compound of interest or, alternatively, by contacting the compound of interest with a hepatocyte or B cell or T cell line) and determining the effect of the compound of interest on the growth of the hepatocytes or differentiation of the B cells or T cell subset activity, as compared to an appropriate control (such as untreated cells or cells treated with a control compound, or carrier, that does not modulate hepatocyte growth or plasma cell differentiation or T cell subset activity). The effect of the test compound on the growth of the hepatocytes or differentiation of plasma cells or T cell subset activity can be determined directly, by monitoring cell proliferation and/or differentiation (as described above) or indirectly, by monitoring one or more markers of cell proliferation and/or differentiation, such as mRNA or protein secretion (as described above) or by monitoring production of Th2 cytokines by T cells.

B. Assays using XBP-1 Deficient Cells

In another embodiment, the invention provides methods for identifying compounds that modulate hepatocyte growth and/or plasma cell differentiation and/or T cell subset activity using cells deficient in XBP-1. As described in the Examples, inhibition of XBP-1 activity (e.g., by disruption of the XBP-1 gene) leads to embryonal hepatocytes with diminished growth rate and prominent apoptosis, leading to embryonic lethality beginning at E12.5. Thus, early (e.g., prior to E12.5) mouse embryonic hepatocytes (or hepatocyte precursors) deficient in XBP-1 can be used identify agents that modulate hepatocyte growth by means, other than modulating XBP-1 itself (i.e., compounds that "rescue" the XBP-1 deficient phenotype). Alternatively, a "conditional knock-out" system, in which the XBP-1 gene is rendered non-functional in a conditional manner, can be used to create XBP-1 deficient hepatocytes (or hepatocyte precursors) for use in screening assays. For example, a tetracycline-regulated system for conditional disruption of a gene as described in WO 94/29442 and U.S. Pat. No. 5,650,298 can be used to create hepatocytes (or hepatocyte precursors), or XBP-1 deficient animals from which hepatocytes (or hepatocyte precursors) can be isolated, that can be rendered XBP-1 deficient in a controlled manner through modulation of the tetracycline concentration in contact with the cells. For assays relating to plasma cell differentiation or T cell subset activity, a similar conditional disruption approach can be used or, alternatively, the RAG-2 deficient blastocyst complementation system can be used to generate mice with lymphoid organs that arise from embryonic stem cells with homozygous mutations of the XBP-1 gene (see Example 2). XBP-1 deficient lymphoid cells (e.g., thymic, splenic and/or lymph node cells) or purified XBP-1 deficient B cells or T cells from such animals can be used in screening assays.

In the screening method, cells deficient in XBP-1 are contacted with a test compound and the growth and/or differentiation and/or activity of the cells is monitored. Modulation of growth of the XBP-1 deficient hepatocytes (or hepatocyte precursors) (as compared to an appropriate control such as, for example, untreated cells or cells treated with a control agent) identifies a test compound as a modulator of hepatocyte growth. Likewise, modulation of differentiation of the XBP-1 deficient plasma cell precursors (as compared to an appropriate control such as, for example, untreated cells or cells treated with a control agent) identifies a test compound as a modulator of plasma cell differentiation. Likewise, modulation of the activity of Th1 versus Th2 cells, e.g., production of Th2 cytokines, (as compared to an appropriate control, such as, for example, untreated cells or cells treated with a control agent) identifies a test compound as a modulator of T cell subset activity. In one embodiment, the test compound is administered directly to a non-human XBP-1 deficient animal, preferably a mouse (e.g., a mouse in which the XBP-1 gene is conditionally disrupted by means described above, or a chimeric mouse in which the lymphoid organs are deficient in XBP-1 as described above), to identify a test compound that modulates the in vivo growth of hepatocytes deficient in XBP-1 or in vivo differentiation of plasma cells deficient in XBP-1 or in vivo T cell subset activity of T cells deficient in XBP-1. In another embodiment, cells deficient in XBP-1 are isolated from the non-human XBP-1 deficient animal, and contacted with the test compound ex vivo to identify a test compound that modulates growth of the isolated hepatocytes deficient in XBP-1 or differentiation of the isolated plasma cells (or plasma cell precursors) deficient in XBP-1 or activity of isolated T cells (e.g., Th2 cytokine production).

Cells deficient in XBP-1 can be obtained from a non-human animals created to be deficient in XBP-1. Preferred non-human animals include monkeys, dogs, cats, mice, rats, cows, horses, goats and sheep. In preferred embodiments, the XBP-1 deficient animal is a mouse. Mice deficient in XBP-1 can be made as described in Example 1. Non-human animals deficient in a particular gene product typically are created by homologous recombination. Briefly, a vector is prepared which contains at least a portion of the XBP-1 gene into which a deletion, addition or substitution has been introduced to thereby alter, e.g, functionally disrupt, the endogenous XBP-1 gene. The XBP-1 gene preferably is a mouse XBP-1 gene. For example, a mouse XBP-1 gene can be isolated from a mouse genomic DNA library using the mouse XBP-1 cDNA as a probe. The mouse XBP-1 gene then can be used to construct a homologous recombination vector suitable for altering an endogenous XBP-1 gene in the mouse genome. In a preferred embodiment, the vector is designed such that, upon homologous recombination, the endogenous XBP-1 gene is functionally disrupted (i.e., no longer encodes a functional protein; also referred to as a "knock out" vector). Alternatively, the vector can be designed such that, upon homologous recombination, the endogenous XBP-1 gene is mutated or otherwise altered but still encodes functional protein (e.g., the upstream regulatory region can be altered to thereby alter the expression of the endogenous XBP-1 protein). In the homologous recombination vector, the altered portion of the XBP-1 gene is flanked at its 5' and 3' ends by additional nucleic acid of the XBP-1 gene to allow for homologous recombination to occur between the exogenous XBP-1 gene carried by the vector and an endogenous XBP-1 gene in an embryonic stem cell. The additional flanking XBP-1 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) Cell 51:503 for a description of homologous recombination vectors). The vector is introduced into an embryonic stem cell line (e.g., by electroporation) and cells in which the introduced XBP-1 gene has homologously recombined with the endogenous XBP-1 gene are selected (see e.g., Li, E. et al (1992) Cell 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E J. Robertson, ed. (ERL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al; WO 92/0968 by Zijlstra et al.; and WO 93/04169 by Berns et al.

In one embodiment of the screening assay, compounds tested for their ability to modulate hepatocyte growth or plasma cell differentiation or T eel subset activity are contacted with XBP-1 deficient cells by administering the test compound to a non-human XBP-1 deficient animal in vivo and evaluating the effect of the test compound on hepatocyte growth or plasma cell differentiation or T cell subset activity in the animal. The test compound can be administered to a non-human XBP-1 deficient animal as a pharmaceutical composition. Such compositions typically comprise the test compound and a pharmaceutically acceptable carrier. As used herein the term "pharmaceutically acceptable carrier" is intended to include any and all solvents, dispersion media, coatings, antibacterial and antifungal compounds, isotonic and absorption delaying compounds, and the like, compatible with pharmaceutical administration. The use of such media and compounds for pharmaceutically active substances is well known hi the art. Except insofar as any conventional media or compound is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid; buffers such as acetates, citrates or phosphates and compounds for the adjustment of tonicity such as sodium chloride or dextrose! pH can be adjusted with acids or bases, such as hydrochloric acid or sodium hydroxide. The parenteral preparation can be enclosed in ampoules., disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as manitol, sorbitol, sodium chloride in the composition. Prolonged absorption of the injectable compositions can be brought about by including in the composition an compound which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilizatioa Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the test compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

In another embodiment, compounds that modulate hepatocyte growth or plasma cell differentiation or T cell subset activity are identified by contacting cells deficient in XBP-1 ex vivo with one or more test compounds, and determining the effect of the test compound on hepatocyte growth or plasma cell differentiation or T cell subset activity. In one embodiment, XBP-1 deficient cells contacted with a test compound ex vivo may be readministered to a subject.

For practicing the screening method ex vivo, cells deficient in XBP-1 can be isolated from a non-human XBP-1 deficient animal or embryo by standard methods and incubated (i.e., cultured) in vitro with a test compound. Hepatocytes and lymphoid cells (e.g., B cells or T cells) can be isolated from XBP-1 deficient animals by standard techniques.

Following contact of the XBP-1 deficient cells with a test compound (either ex vivo or in vivo), the effect of the test compound on the growth of the hepatocytes cells or differentiation of plasma cells or activity of T cell subsets can be determined by any one of a variety of suitable methods, including light microscopic analysis of the cells, histochemical analysis of the cells, analysis of the proliferative capacity of the cells or analysis of Th2 cytokine production. For example, to monitor hepatocyte proliferation, one can monitor radiolabeled thymidine uptake, BrdU uptake, TUNEL staining (for monitoring apoptosis) or induction of transcription of immediate early genes (see Example 1). To monitor plasma cell differentiation, one can monitor, for example, immunoglobulin secretion or upregulation of Syndecan-1 expression (see Example 2). To monitor T cell subset activity, one can monitor, for example, Th2 versus Th2 cytokine production by ELISA (see Example 4). A test compound is identified as a modulator of hepatocyte growth or plasma cell differentiation or T cell subset activity based on its ability to modulate the growth of XBP-1 deficient hepatocytes or differentiation of XBP-1 B cells of the activity of T cell subsets, as compared to an appropriate control (such as untreated cells or cells treated with a control compound, or carrier, that does not modulate hepatocyte growth or plasma cell differentiation or T cell subset activity).

A variety of test compounds can be evaluated using the screening assays described in subsections A and B above. In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J Am. Chem. Soc.* 114:10987; DeWitt et al. (1993). *Proc. Natl. Acad. Sci. USA* 90:6909) peptoids (Zuckennann. (1994). *JMed Chem.* 37:2678) oligocarbamates (Cho et al. (1993). *Science.* 261:1303-), and hydantoins (DeWitt et al. supra). An approach for the synthesis of molecular libraries of small organic molecules with a diversity of 104-105 as been described (Carell et al. (1994). Angew. *Chem. Int. Ed Engl.* 33:2059-Carell et al. (1994). Angew. *Chem. Int. Ed. Engl.* 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). Other exemplary methods for the synthesis of molecular libraries can be found in the art, for example in: Erb et al. (1994). *Proc. Natl. Acad. Sci. USA* 91:11422; Horwell et al. (1996) *Immunopharmacology* 33:68; and in Gallop et al. (1994); *JMed Chem.* 37:1233.

Libraries of compounds may be presented in solution (e.g., Houghten (1992) *Biotechniques* .13:412-421), or on beads (Lam (1991) *Nature* 354:82-84), chips (Fodor (1993) *Nature* 364:555-556), bacteria (Ladner U.S. Pat. No. 5,223, 409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *JMol. Biol.* 222:301-310); In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Methods for Modulating Hepatocyte Growth or Plasma Cell Differentiation or T Cell Subset Activity hi another aspect, the invention features a method for modulating growth of hepatocytes or differentiation of plasma cells or activity of T cell subsets by contacting hepatocytes or B cells (plasma cell precursors) or T cells (or T cell precursors) with a modulator of XBP-1 activity such that growth of the hepatocytes or differentiation of the plasma cells or activity of T cell subsets is modulated The modulatory methods of the invention are of particular interest for use in expanding populations of hepatocytes or plasma cells or T cells subsets in vitro for administration to a subject with insufficient hepatocytes or plasma cells or T cell subsets.

The invention also allows for modulation of aberrant hepatocyte growth or plasma cell differentiation or T cell subset activity in a subject in vivo, by administering to the subject a therapeutically effective amount of a modulator of XBP-1 activity such that aberrant hepatocyte growth or plasma cell differentiation or T cell subset activity in a subject is modulated. The term "subject" is intended to include living organisms but preferred subjects are mammals. Examples of subjects include humans, monkeys, dogs, cats, mice, rats cows, horses, goats, and sheep. Modulation of XBP-1 activity, therefore, provides a means to regulate aberrant hepatocyte growth or plasma cell differentiation or T cell subset activity in various disease states. In one embodiment, for stimulation of hepatocyte growth or plasma cell differentiation or Th2 cell activity, the modulator stimulates XBP-1 activity. In another embodiment, to inhibit hepatocyte growth or plasma cell differentiation or Th2 cell activity, the modulator inhibits XBP-1 activity.

Identification of compounds that modulate the growth of hepatocytes or plasma cell differentiation or T cell subset activity by modulating XBP-1 activity allows for selective manipulation of hepatocytes or plasma cells or T helper cells in a variety of clinical situations using the modulatory methods of the invention The stimulatory methods of the invention (i.e., methods that use a stimulatory agent) result in increased activity of XBP-1, which stimulates hepatocyte growth and plasma cell differentiation and Th2 cell activity. In contrast, the inhibitory methods of the invention (i.e., methods that use an inhibitory agent) inhibit the activity of XBP-1 and inhibit hepatocyte growth and plasma cell differentiation and Th2 cell activity, as demonstrated in the Examples.

Thus, to treat a disorder wherein inhibition of hepatocyte growth or plasma cell differentiation or Th2 cell activity is beneficial, an inhibitory method of the invention is selected such that XBP-1 activity is inhibited. Examples of disorders in which these inhibitory methods may be useful include hepatocellular carcinoma, multiple myeloma, autoimmune diseases characterized by the production of pathogenic autoantibodie, and disorders involving unwanted Th2 cell activity (discussed further below). Alternatively, to treat a disorder wherein stimulation of hepatocyte growth or plasma cell differentiation or Th2 cell activity is beneficial, a stimulatory method of the invention is selected such that XBP-1 activity is upregulated. Examples of situations in which these stimulatory methods may be useful include hepatic injury, hepatic failure due to hepatic disease (e.g., viral infection, such as hepatitis), hepatic failure due to hepatic toxins (such as cirrhosis), immunodeficiency disorders characterized by insufficient antibody production, disorders involving unwanted Th1 cell activity (discussed further below), as well as use in improving humor responses to pathogens in a subject and for improving the efficacy of vaccination in a subject. Application of the modulatory methods of the invention to the treatment of a disorder may result in cure of the disorder, a decrease in the type or number of symptoms associated with the disorder, either in the long term or short term (i.e., amelioration of the condition) or simply a transient beneficial effect to the subject.

Application of the immunomodulatory methods of the invention is described in further detail below.

A. Inhibitory Compounds

Since inhibition of XBP-1 activity is associated with inhibition of hepatocyte growth and plasma cell differentiation and Th2 cell activity, to inhibit hepatocyte growth or plasma cell differentiation or Th2 cell activity, cells are contacted with an agent that inhibits XBP-1 activity. Cells may be contacted with the agent in vitro and then the cells can be administered to a subject or, alternatively, the agent may be administered to the subject. The methods of the invention using XBP-1 inhibitory compounds can be used in the treatment of disorders in which hepatocyte growth or plasma cell differentiation or Th2 cell activity is enhanced, stimulated, upregulated or the like. For example, hepatocellular carcinoma is associated with increased proliferation of hepatocytes, whereas multiple myelomas and certain autoimmune diseases are associated with increased immunoglobulin production by plasma cells. Accordingly, preferred disorders for treatment using an inhibitory compound of the invention include hepatocellular carcinoma, multiple myeloma, autoimmune disorders characterized by increased immunoglobulin production and disorders involving unwanted Th2 cell activity (discussed further below).

Inhibitory compounds of the invention can be, for example, intracellular binding molecules that act to specifically inhibit the expression or activity of XBP-1. As used herein, the term "intracellular binding molecule" is intended to include molecules that act intracellularly to inhibit the expression or activity of a protein by binding to the protein or to a nucleic acid (e.g., an mRNA molecule) that encodes the protein. Examples of intracellular binding molecules, described in further detail below, include antisense nucleic acids, intracellular antibodies, peptidic compounds that inhibit the interaction of XBP-1 with a target molecule and chemical agents that specifically inhibit XBP-1 activity.

i. Antisense Nucleic Acid Molecules

In one embodiment, an inhibitory compound of the invention is an antisense nucleic acid molecule that is complementary to a gene encoding XBP-1, or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, *Reviews—Trends in Genetics*, Vol. 1(1) 1986; Askari, F. K. and McDonnell, W. M. (1996) *N. Eng. JMed.* 334:316-318; Bennett, M. R. and Schwartz, S. M. (1995) *Circulation* 92:1981-1993; Mercola, D. and Cohen, J. S. (1995) *Cancer Gene Ther.* 2:47-59; Rossi, J. J. (1995) *Br. Med Bull.* 51:217-225; Wagner, R. W. (1994) *Nature* 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Given the known nucleotide sequence for the coding strand of the XBP-1 gene (and thus the known sequence of the XBP-1 mRNA), antisense nucleic acids of the invention can be designed according to the rules of Watson and Crick base pairing. The antisense nucleic acid molecule can be complementary to the entire coding region of a XBP-1 mRNA, but more preferably is an oligonucleotide which is antisense to only a portion of the coding or noncoding region of a XBP-1 mRNA For example, the antisense oligonucleotide can be complementary to the region surrounding the translation start site of a XBP-1 mRNA An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, S'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. To inhibit XBP-1 expression in cells in culture, one or more antisense oligonucleotides can be added to cells in culture media.

Alternatively, an antisense nucleic acid can be produced biologically using an expression vector into which all or a portion of XBP-1 cDNA has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA The antisense expression vector is prepared according to standard recombinant DNA methods for constructing recombinant expression vectors, except that the XBP-1 cDNA (or portion thereof) is cloned into the vector in the antisense orientation. The antisense expression vector can be in the form of, for example, a recombinant plasmid, phagemid or attenuated virus. The antisense expression vector is introduced into cells using a standard transfection technique.

The antisense nucleic acid molecules of the invention are typically administered to a subject or generated in situ such that they hybridize with or bind to cellular mRNA and/or genomic DNA encoding a XBP-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigea The antisense nucleic acid molecule can also be delivered to cells using the vectors described herein. To achieve sufficient intracellular concentrations of the antisense molecules, vector constructs in which the antisense nucleic acid molecule is placed under the control of a strong pol n or pol III promoter are preferred.

In yet another embodiment, the antisense nucleic acid molecule of the invention is an a-anomeric nucleic acid molecule. An a-anomeric nucleic acid molecule forms specific double-stranded hybrids with complementary RNA in which, contrary to the usual P-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEES Lett.* 215: 327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave XBP-1 mRNA transcripts to thereby inhibit translation of XBP-1 mRNAs. A ribozyme having specificity for a XBP-1-encoding nucleic acid can be designed based upon the nucleotide sequence of the XBP-1 cDNA. For example, a derivative of a *Tetrahymena* L-19 IVS RNA can be. constructed hi which the nucleotide sequence of the active site is complementary to the nucleotide sequence to be cleaved in a XBP-1-encoding mRNA See, e.g., Cech et al. U.S. Pat. No. 4,987,071 and Cech et al. U.S. Pat. No. 5,116,742. Alternatively, XBP-1 mRNA can be used to select a catalytic RNA having a specific ribonuclease activity from a pool of RNA molecules. See, e.g., Bartel, D. and Szostak, J. W. (1993) *Science* 261:1411-1418.

Alternatively, XBP-1 gene expression can be inhibited by targeting nucleotide sequences complementary to the regulatory region of an XBP-1 gene (e.g., an XBP-1 promoter and/or enhancer) to form triple helical structures that prevent transcription of an XBP-1 gene in target cells. See generally, Helene, C. (1991) *Anticancer Drug Des.* 6(6):569-84; Helene, C. etal. (1992) *Ann. N. YAcad. Sci.* 660:27-36; and Maher, L. J. (1992) *Bioassays* 14(12):807-15.

ii. Intracellular Antibodies

Another type of inhibitory compound that can be used to inhibit the expression and/or activity of XBP-1 protein in a cell is an intracellular antibody specific for XBP-1 discussed herein. The use of intracellular antibodies to inhibit protein function in a cell is known in the art (see e.g, Carlson, J. R. (1988) *Mol. Cell. Biol.* 8:2638-2646; Biocca, S. et al. (1990) *EMBO J.* 9:101-108; Werge, T. M. et al (1990) *FEBS Letters* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Bio/Technology* 12:396-399; Chen, S-Y. et al. (1994) *Human Gene Therapy* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994)/. *Biol. Chem.* 269:23931-23936; Beerli, R. R. et al. (1994) *Biochem. Biophys. Res. Commun.* 204:666-672; Mhashilkar, A. M. et al. (1995) *EMBO J* 14:1542-155 1; Richardson,] M. et al. (1995) *Proc. Natl. Acad. Sci. USA* 92:3137-3141; PCT Publication No. WO 94/02610 by Marasco et al; and PCT Publication No. WO 95/03832 by Duan et al).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of transcription factor activity according to the inhibitory methods of the invention, preferably an intracellular antibody that specifically binds the transcription factor is expressed within the nucleus of the cell. Nuclear expression of an intracellular antibody can be accomplished by removing from the antibody light and heavy chain genes those nucleotide sequences that encode the N-terminal hydrophobic leader sequences and adding nucleotide sequences encoding a nuclear localization signal at either the N- or C-terminus of the light and heavy chain genes (see e.g., Biocca, S. et al. (1990) *EMBO J.* 9:101-108; Mhashilkar, A. M. et al (1995) *EMBO J.* 14:1542-15 51). A preferred nuclear localization signal to be used for nuclear targeting of the intracellular antibody chains is the nuclear localization signal of SV40 Large T antigen (see Biocca, S. et al (1990) *EMBO J.* 9:101-108; Mhashilkar, A. M. et al. (1995)*EMBO J.* 14:1542-1551).

To prepare an intracellular antibody expression vector, antibody light and heavy chain cDNAs encoding antibody chains specific for the target protein of interest, e.g., XBP-1 protein, is isolated, typically from a hybridoma that secretes a monoclonal antibody specific for XBP-1 protein. Anti-XBP-1 protein antibodies can be prepared by immunizing a suitable subject, (e.g., rabbit, goat, mouse or other mammal) with a XBP-1 protein immunogen. An appropriate immunogenic preparation can contain, for examples, recombinantly expressed XBP-1 protein or a chemically synthesized XBP-1 peptide. The preparation can further include an adjuvant, such as Freund's complete or incomplete adjuvant, or similar immunostimulatory compound. Antibody-producing cells can be obtained from the subject and used to prepare monoclonal antibodies by standard techniques, such as the hybridoma technique originally described by Kohler and Milstein (1975, *Nature* 256:495-497) (see also, Brown et al. (1981) *J Immunol* 127:539-46; Brown et al. (1980) *J. Biol Chem* 255:4980-83; Yeh et al. (1976) *PNAS* 76:2927-31; and Yeh et al. (1982) *Int. J Cancer* 29:269-75). The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J Biol. Med,* 54:387-402; M. L. Gefter et al. (1977) *Somatic Cell Genet.,* 3:231-36). Briefly, an immortal cell line (typically a myeloma) is fused to lymphocytes (typically splenocytes) from a mammal immunized with a XBP-1 protein immunogen as described above, and the culture supernatants of the resulting hybridoma cells are screened to identify a hybridoma producing a monoclonal antibody that binds specifically to the XBP-1 protein. Any of the many well known protocols used for fusing lymphocytes and immortalized cell lines can be applied for the purpose of generating an anti-XBP-1 protein monoclonal antibody (see, e.g., G. Galfre et al. (1977) *Nature* 266:5 50-52; Gefter et al. *Somatic Cell Genet.*, cited supra; Lerner, *Yale J. Biol. Med*, cited supra; Kenneth, *Monoclonal Antibodies*, cited supra). Moreover, the ordinary skilled artisan will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Agl4 myeloma lines. These myeloma lines are available from the American Type Culture Collection (ATCC), Rockville, Md. Typically, HAT-sensitive mouse myeloma cells are fused to mouse splenocytes using polyethylene glycol ("PEG". Hybridoma cells resulting from the fusion are then selected using HAT medium, which kills unfused and unproductively fused myeloma cells (unfused splenocytes die after several days because they are not transformed). Hybridoma cells producing a monoclonal antibody that specifically binds the XBP-1 protein are identified by screening the hybridoma culture supernatants for such antibodies, e.g., using a standard ELISA assay.

Alternative to preparing monoclonal antibody-secreting hybridomas, a monoclonal antibody that binds to XBP-1 can be identified and isolated by screening a recombinant combinatorial immunoglobulin library (e.g., an antibody phage display library) with the protein, or a peptide thereof, to thereby isolate immunoglobulin library members that bind specifically to the protein. Kits for generating and screening phage display libraries are commercially available (e.g., the *Pharmacia Recombinant Phage Antibody System*, Catalog No. 27-9400-01; and the Stratagene SurfZAP™ Phage Display Kit, Catalog No. 240612). Additionally, examples of methods and compounds particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et at. International Publication WO 92/20791; Markland et at. International Publication No. WO 92/15679; Breitling et al. International Publication WO 93/01288; McCafferty et al. International Publication No. WO 92/01047; Garrard et al. International Publication No. WO 92/09690; Fuchs et al. (1991) *Bio/Technology* 9:1370-1372; Hay et al. (1992) *Hum Antibod hybridomas* 3:81-85; Huse et al. (1989) *Science* 246:1275-1281; Griffiths et al. (1993) *EMBO J* 12:725-734; Hawkins et al. (1992) *JMolBiol* 226: 889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et at. (1991) *Nuc Acid Res* 19:4133-4137; Barbas et al. (1991) *PNAS* 88:7978-7982; and McCafferty et al. *Nature (*1990) 348: 552-554.

Once a monoclonal antibody of interest specific for XBP-1 has been identified (e.g., either a hybridoma-derived monoclonal antibody or a recombinant antibody from a combinatorial library, including monoclonal antibodies to XBP-1 that are already known in the art), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. As discussed above, the sequences encoding the hydrophobic leaders of the light and heavy chains are removed and sequences encoding a nuclear localization signal (e.g., from SV40 Large T antigen) are linked in-frame to sequences encoding either the amino- or carboxy terminus of both the light and heavy chains. The expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH I region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., (G^Ser)^) and expressed as a single chain molecule. To inhibit transcription factor activity in a cell, the expression vector encoding the XBP-1-specific intracellular antibody is introduced into the cell by standard transfection methods as described hereinbefore.

iii. XBP-1-Derived Peptidic Compounds

In another embodiment, an inhibitory compound of the invention is a peptidic compound derived from the XBP-1 amino acid sequence. In particular, the inhibitory compound comprises a portion of XBP-1 (or a mimetic thereof) that mediates interaction of XBP-1 with a target molecule such that contact of XBP-1 with this peptidic compound competitively inhibits the interaction of XBP-1 with the target molecule. For example, the peptide compound can be designed based on the b-Zip region of XBP-1 that mediates interaction of XBP-1 with c-Fos.

The peptidic compounds of the invention can be made intracellularly in cells by introducing into the cells an expression vector encoding the peptide. Such expression vectors can be made by standard techniques using oligonucleotides that encode the amino acid sequence of the peptidic compound. The peptide can be expressed in intracellularly as a fusion with another protein or peptide (e.g., a GST fusion). Alternative to recombinant synthesis of the peptides in the cells, the peptides can be made by chemical synthesis using standard peptide synthesis techniques. Synthesized peptides can then be introduced into cells by a variety of means known in the art for introducing peptides into cells (e.g., liposome and the like).

Other inhibitory agents that can be used to specifically inhibit the activity of an XBP-1 protein are chemical compounds that directly inhibit XBP-1 activity or inhibit the interaction between XBP-1 and target molecules. Such compounds can be identified using screening assays that select for such compounds, as described in detail above.

B. Stimulatory Compound

Since downregulation of XBP-1 activity is associated with decreased hepatocyte growth, plasma cell differentiation and Th2 cell activity, a compound that specifically stimulates XBP-1 activity can be used to stimulate hepatocyte growth or plasma cell differentiation or Th2 cell activity. In the stimulatory methods of the invention, a subject is treated with a stimulatory compound that stimulates expression and/or activity of XBP-1. The methods of the invention using XBP-1 stimulatory compounds can be used in the treatment of disorders in which hepatocyte growth or plasma cell differentiation or Th2 cell activity is inhibited, blocked, downregulated or the like. Disorders associated with decreased hepatocyte growth that may benefit from the stimulatory methods of the invention include hepatic injury, hepatic failure due to hepatic disease (e.g., viral infection, such as hepatitis) and hepatic failure due to hepatic toxins (e.g., cirrhosis). Disorders associated with decreased plasma cell differentiation that may benefit from the simulatory methods of the invention include immunodeficiency disorders characterized by insufficient antibody production. Moreover, the methods for stimulating plasma cell differentiation are of general use in the stimulation of humoral immune responses to pathogens in a subject and in improved antibody responses during vaccination of a subject. Furthermore, methods for stimulating Th2 cell activity may be beneficial in disorders involving unwanted Th1 cell activity (to thereby shift the balance of Th1 versus Th2 cells to the Th2 pathway) or in disorders in which increased Th2 cell activity is desireable (discussed further below).

Examples of stimulatory compounds include active XBP-1 protein, expression vectors encoding XBP-1 and chemical agents that specifically stimulate XBP-1 activity.

A preferred stimulatory compound is a nucleic acid molecule encoding XBP-1, wherein the nucleic acid molecule is introduced into the subject in a form suitable for expression of the XBP-1 protein in the cells of the subject. For example, an XBP-1 cDNA (full length or partial XBP-1 cDNA sequence) is cloned into a recombinant expression vector and the vector is transfected into cells using standard molecular biology techniques. The XBP-1 cDNA can be obtained, for example, by amplification using the polymerase chain reaction (PCR) or by screening an appropriate cDNA library. The nucleotide sequences of XBP-1 cDNA is known in the art and can be used for the design of PCR primers that allow for amplification of a cDNA by standard PCR methods or for the design of a hybridization probe that can be used to screen a cDNA library using standard hybridization methods.

Following isolation or amplification of XBP-1 cDNA, the DNA fragment is introduced into a suitable expression vector, as described above. Nucleic acid molecules encoding XBP-1 hi the form suitable for expression of the XBP-1 in a host cell, can be prepared as described above using nucleotide sequences known in the art The nucleotide sequences can be used for the design of PCR primers that allow for amplification of a cDNA by standard PCR methods or for the design of a hybridization probe that can be used to screen a cDNA library using standard hybridization methods.

Another form of a stimulatory compound for stimulating expression of XBP-1 in a cell is a chemical compound that specifically stimulates the expression or activity of endogenous XBP-1 in the cell. Such compounds can be identified using screening assays that select for compounds that stimulate the expression or activity of XBP-1 as described herein.

The method of the invention for modulating aberrant hepatocyte growth or plasma cell differentiation or T cell subset activity in a subject can be practiced either in vitro or in vivo. For practicing the method in vitro, cells can be obtained from a subject by standard methods and incubated (i.e., cultured) in vitro with a stimulatory or inhibitory compound of the invention to stimulate or inhibit, respectively, the activity of XBP-1. Methods for isolating hepatocytes, hepatocyte precursors, plasma cells, plasma cell precursors (B cells), T cells or T cell precursors are known in the art.

Cells treated in vitro with either a stimulatory or inhibitory compound can be administered to a subject to influence the growth of hepatocytes or differentiation of plasma cells or T cell subset activity in the subject. For example, cells can be isolated from a subject, expanded in number in vitro by stimulating XBP-1 activity in the cells using a stimulatory agent (thereby stimulating growth of hepatocytes or differentiation of B cells into plasma cells or Th2 cell activity), and then the cells can be readministered to the same subject, or another subject tissue compatible with the donor of the cells. Accordingly, in another embodiment, the modulatory method of the invention comprises culturing hepatocytes or B cells or T cells in vitro with a XBP-1 modulator and further comprises administering the cells to a subject to thereby modulate hepatocyte growth or plasma cell differentiation or T cell subset activity in a subject. Upon culture in vitro, the cells can differentiate in to mature hepatocytes or plasma cells or Th2 cells, respectively, and thus the methods encompass administering this mature hepatocytes or plasma cells or Th2 cells to the subject. For administration of cells to a subject, it may be preferable to first remove residual compounds in the culture from the cells before administering them to the subject. This can be done for example by gradient centrifugation of the cells or by washing of the tissue. For further discussion of ex vivo genetic modification of cells followed by readministration to a subject, see also U.S. Pat. No. 5,399,346 by W. F. Anderson et al.

In other embodiments, a stimulatory or inhibitory compound is administered to a subject in vivo, such as administration of hepatocytes directly to the liver site of a subject or administration of plasma cells into the circulation or lymphoid system of a subject. For stimulatory or inhibitory agents that comprise nucleic acids (e.g., recombinant expression vectors encoding XBP-1, antisense RNA, intracellular antibodies or XBP-1-derived peptides), the compounds can be introduced into cells of a subject using methods known in the art for introducing nucleic acid (e.g., DNA) into cells in vivo. Examples of such methods include:

Direct Injection: Naked DNA can be introduced into cells in vivo by directly injecting the DNA into the cells (see e.g., Acsadi et al. (1991) *Nature* 332:815-818: Wolffe? al. (1990) *Science* 247:1465-1468). For example, a delivery apparatus (e.g., a "gene gun") for injecting DNA into cells in vivo can be used. Such an apparatus is commercially available (e.g., from BioRad).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J Biol. Chem.* 263:14621; Wilson et al. (1992)*J. Biol. Chem.* 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126).

Retroviruses: Defective retroviruses are well characterized for use in gene transfer for gene therapy purposes (for a review see Miller, A. D. (1990) *Blood* 76:271). A recombinant retro virus can be constructed having a nucleotide sequences of interest incorporated into the retro viral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*. Ausubel, P. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψCrip, vl/Cre, vl/2 and vl/Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *Bio Techniques* 6:616; Rosenfeld et al. (1991) *Science* 252:431-434; and Rosenfeld et al (1992) *Cell* 68:143-155. Suitable adenoviral vectors derived from the adenovirus strain Ad type 5 d!324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al (1992)*Proc. Natl. Acad. Sci. USA* 89:6482-6486), hepatocytes (Herz and Gerard (1992)*Proc. Natl. Acad. Sci. USA* 90:2812-2816) and muscle cells (Quantin et al. (1992) *Proc. Natl. Acad Sci. USA* 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al cited supra; Haj-Ahmand and Graham (1986) *J Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro, and Immunol.* (1992) 158:97-1291 It is also one of the few viruses that may integrate its DNA into non-dividing cells, and exhibits a high frequency of stable integration (see for example Flotte et al. (1992) *Am. J Respir. Cell. Mol. Biol.* 7:349-356; Samulski et al. (1989) *J Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J Virol.* 51:611-619; and Flotte et al. (1993) *J Biol. Chem.* 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay.

If the stimulatory or inhibitory compounds are chemical compounds that modulate XBP-1 activity, the stimulatory or inhibitory compounds can be administered to a subject as a pharmaceutical composition. Such compositions typically comprise the stimulatory or inhibitory compounds and a pharmaceutically acceptable carrier. Pharmaceutically acceptable carriers and methods of administration to a subject are described above.

With regard to the methods of the invention for modulating T cell subset activity by modulation of XBP-1 activity, numerous disease conditions associated with a predominant Th1 or Th2-type response have been identified and could benefit from modulation of the type of response mounted in the individual suffering from the disease condition. Application of the immunomodulatory methods of the invention to such diseases is described in further detail below.

A. Allergies

Allergies are mediated through IgE antibodies whose production is regulated by the activity of Th2 cells and the cytokines produced thereby. In allergic reactions, IL-4 is produced by Th2 cells, which further stimulates production of IgE antibodies and activation of cells that mediate allergic reactions, i e., mast cells and basophils. IL-4 also plays an important role in eosinophil mediated inflammatory reactions. Accordingly, the inhibitory methods of the invention can be used to inhibit the production of Th2-associated cytokines, and in particular IL-4, in allergic patients as a means to downregulate production of pathogenic IgE antibodies. An inhibitory agent may be directly administered to the subject or cells (e.g., Thp cells or Th2 cells) may be obtained from the subject, contacted with an inhibitory agent ex vivo, and readministered to the subject. Moreover, in certain situations it may be beneficial to coadminister to the subject the allergen together with the inhibitory agent or cells treated with the inhibitory agent to inhibit (e.g., desensitize) the allergen-specific response. The treatment may be further enhanced by administering other Th1-promoting agents, such as the cytokine IL-12 or antibodies to Th2-associated cytokines (e.g. anti-IL-4 antibodies), to the allergic subject in amounts sufficient to further stimulate a Th1-type response.

B. Cancer

The expression of Th2-promoting cytokines has been reported to be elevated in cancer patients (see e.g., Yamamura, M., et al. (1993) *J. Clin. Invest.* 91:1005-1010; Pisa, P., et al. (1992) *Proc. Natl. Acad. Sci USA* 89:7708-7712) and malignant disease is often associated with a shift from Th1 type responses to Th2 type responses along with a worsening of the course of the disease. Accordingly, the inhibitory methods of the invention can be used to inhibit the production of Th2-associated cytokines in cancer patients, as a means to counteract the Th1 to Th2 shift and thereby promote an ongoing Th1 response in the patients to ameliorate the course of the disease. The inhibitory method can involve either direct administration of an inhibitory agent to a subject with cancer or ex vivo treatment of cells obtained from the subject (e.g., Thp or Th2 cells) with an inhibitory agent followed by readministration of the cells to the subject. The treatment may be further enhanced by administering other Th1-promoting agents, such as the cytokine IL-12 or antibodies to Th2-associated cytokines (e.g. anti-IL-4 antibodies), to the recipient in amounts sufficient to further stimulate a Th1-type response.

C. Infectious Diseases

The expression of Th2-promoting cytokines also has been reported to increase during a variety of infectious diseases, including HIV infection, tuberculosis, leishmaniasis, schistosomiasis, filarial nematode infection and intestinal nematode infection (see e.g.; Shearer, G. M. and Clerici, M. (1992) *Prog. Chem. Immunol.* 54:21-43; Clerici, M and Shearer, G. M. (1993) *Immunology Today* 14:107-111; Fauci, A. S. (1988) *Science* 239:617623; Locksley, R. M. and Scott, P. (1992) *Immunoparasitology Today* 1:A58-A61; Pearce, E. J., et al. (1991) *J. Exp. Med.* 173:159-166; Grzych, J-M., et al. (1991) *J. Immunol.* 141:1322-1327; Kullberg, M. C., et al. (1992) *J. Immunol.* 148:3264-3270; Bancroft, A. J., et al. (1993)/. *Immunol.* 150:1395-1402; Pearlman, E., et al. (1993) *Infect. Immun.* 61:1105-1112; Else, K. J., et al. (1994)/. *Exp. Med.* 179:347-351) and such infectious diseases are also associated with a Th1 to Th2 shift in the immune response. Accordingly, the inhibitory methods of the invention can be used to inhibit the production of Th2-associated cytokines in subjects with infectious diseases, as a means to counteract the Th1 to Th2 shift and thereby promote an ongoing Th1 response in the patients to ameliorate the course of the infection. The inhibitory method can involve either direct administration of an inhibitory agent to a subject with an infectious disease or ex vivo treatment of cells obtained from the subject (e.g., Thp or Th2 cells) with an inhibitory agent followed by readministration of the cells to the subject. The treatment may be further enhanced by administering other Th1-promoting agents, such as the cytokine IL-12 or antibodies to Th2-associated cytokines (e.g., anti-IL-4 antibodies), to the recipient in amounts sufficient to further stimulate a Th1-type response.

D. Autoimmune Diseases

The stimulatory methods of the invention can be used therapeutically in the treatment of autoimmune diseases that are associated with a Th2-type dysfunction. Many autoimmune disorders are the result of inappropriate activation of T cells that are reactive against self tissue and that promote the production of cytokines and autoantibodies involved in the pathology of the diseases. Modulation of T helper-type responses can have an effect on the course of the autoimmune disease. For example, in experimental allergic encephalomyelitis (EAE), stimulation of a Th2-type response by administration of IL-4 at the time of the induction of the disease diminishes the intensity of the autoimmune disease (Paul, W. E., et al. (1994) *Cell* 76:241-251). Furthermore, recovery of the animals from the disease has been shown to be associated with an increase in a Th2-type response as evidenced by an increase of Th2-specific cytokines (Koury, S. I, et al. (1992) *J. Exp. Med.* 176:1355-1364). Moreover, T cells that can suppress EAE secrete Th2-specific cytokines (Chen, C., et al. (1994) *Immunity* 1:147-154). Since stimulation of a Th2-type response in EAE has a protective effect against the disease, stimulation of a Th2 response in subjects with multiple sclerosis (for which EAE is a model) is likely to be beneficial therapeutically.

Similarly, stimulation of a Th2-type response in type I diabetes in mice provides a protective effect against the disease. Indeed, treatment of NOD mice with IL-4 (which promotes a Th2 response) prevents or delays onset of type I diabetes that normally develops in these mice (Rapoport, M. J., et al. (1993) *J. Exp. Med.* 178:87-99). Thus, stimulation of a Th2 response in a subject suffering from or susceptible to diabetes may ameliorate the effects of the disease or inhibit the onset of the disease.

Yet another autoimmune disease in which stimulation of a Th2-type response may be beneficial is rheumatoid arthritis (RA). Studies have shown that patients with rheumatoid arthritis have predominantly Th1 cells in synovial tissue (Simon, A. K., et al., (1994) *Proc. Natl. Acad. Sci USA* 91:8562-8566). By stimulating a Th2 response in a subject with RA, the detrimental Th1 response can be concomitantly downmodulated to thereby ameliorate the effects of the disease.

Accordingly, the stimulatory methods of the invention can be used to stimulate production of Th2-associated cytokines in subjects suffering from, or susceptible to, an autoimmune disease in which a Th2-type response is beneficial to the course of the disease. The stimulatory method can involve either direct administration of a stimulatory agent to the subject or ex vivo treatment of cells obtained from the subject (e.g., Thp, Th1 cells, B cells, non-lymphoid cells) with a stimulatory agent followed by readministration of the cells to the subject. The treatment may be further enhanced by administering other Th2-promoting agents, such as IL-4 itself or antibodies to Th1-associated cytokines, to the subject in amounts sufficient to further stimulate a Th2-type response.

In contrast to the autoimmune diseases described above in which a Th2 response is desirable, other autoimmune diseases may be ameliorated by a Th1-type response. Such diseases can be treated using an inhibitory agent of the invention (as described above for cancer and infectious diseases). The treatment may be further enhanced by administrating a Th1-promoting cytokine (e.g., IFN-y) to the subject in amounts sufficient to further stimulate a Th1-type response.

The efficacy of agents for treating autoimmune diseases can be tested in the above described animal models of human diseases (e.g., EAE as a model of multiple sclerosis and the NOD mice as a model for diabetes) or other well characterized animal models of human autoimmune diseases. Such animal models include the mrl/lpr/lpr mouse as a model for lupus erythematosus, murine collagen-induced arthritis as a model for rheumatoid arthritis, and murine experimental myasthenia gravis (see Paul ed., *Fundamental Immunology*, Raven Press, New York, 1989, pp. 840-856). A modulatory (i.e., stimulatory or inhibitory) agent of the invention is administered to test animals and the course of the disease hi the test animals is then monitored by the standard methods for the particular model being used. Effectiveness of the modulatory agent is evidenced by amelioration of the disease condition in animals treated with the agent as compared to untreated animals (or animals treated with a control agent).

Non-limiting examples of autoimmune diseases and disorders having an autoimmune component that may be treated according to the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

E. Transplantation

While graft rejection or graft acceptance may not be attributable exclusively to the action of a particular T cell subset (i.e., Th1 or Th2 cells) in the graft recipient (for a discussion see Dallman, M. J. (1995) *Curr. Opin. Immunol.* 7:632-638), numerous studies have implicated a predominant Th2 response in prolonged graft survival or a predominant Th2 response in graft rejection. For example, graft acceptance has been associated with production of a Th2 cytokine pattern and/or graft rejection has been associated with production of a Th1 cytokine pattern (see e.g., Takeuchi, T. et al. (1992) *Transplantation* 53:1281-1291; Tzakis, A. G. et al. (1994) *J, Pediatr. Surg* 29:754-756; Thai, N. L. et al. (1995) *Transplantation* 59:274-281). Additionally, adoptive transfer of cells having a Th2 cytokine phenotype prolongs skin graft survival (Maeda, H. et al. (1994) *Int. Immunol.* 6:855-862) and reduces graft-versus-host disease (Fowler, D. H. et al. (1994) *Blood* 84:3540-3549; Fowler, D. H. et al. (1994) *Prog. Clin. Biol. Res.* 389:533-540). Still further, administration of IL-4, which promotes Th2 differentiation, prolongs cardiac allograft survival (Levy, A. E. and Alexander, J. W. (1995) *Transplantation* 60:405-406), whereas administration of IL-12 in combination with anti-IL-10 antibodies, which promotes Th1 differentiation, enhances skin allograft rejection (Gorczynski, R. M. et al. (1995) *Transplantation* 60:1337-1341).

Accordingly, the stimulatory methods of the invention can be used to stimulate production of Th2-associated cytokines in transplant recipients to prolong survival of the graft. The stimulatory methods can be used both in solid organ transplantation and in bone marrow transplantation (e.g., to inhibit graft-versus-host disease). The stimulatory method can involve either direct administration of a stimulatory agent to the transplant recipient or ex vivo treatment of cells obtained from the subject (e.g., Thp, Th1 cells, B cells, non-lymphoid cells) with a stimulatory agent followed by readministration of the cells to the subject. The treatment may be further enhanced by administering other Th2-promoting agents, such as IL-4 itself or antibodies to Th1-associated cytokines, to the recipient in amounts sufficient to further stimulate a Th2-type response.

In addition to the foregoing disease situations, the modulatory methods of the invention also are useful for other purposes. For example, the stimulatory methods of the invention (i.e., methods using a stimulatory agent) can be used to stimulate production of Th2-promoting cytokines (e.g., IL-4) in vitro for commercial production of these cytokines (e.g., cells can be contacted with the stimulatory agent in vitro to stimulate IL-4 production and the IL-4 can be recovered from the culture supernatant, further purified if necessary, and packaged for commercial use).

Furthermore, the modulatory methods of the invention can be applied to vaccinations to promote either a Th1 or a Th2 response to an antigen of interest in a subject. That is, the agents of the invention can serve as adjuvants to direct an immune response to a vaccine either to a Th1 response or a Th2 response. For example, to stimulate an antibody response to an antigen of interest (i e., for vaccination purposes), the antigen and a stimulatory agent of the invention can be coadministered to a subject to promote a Th2 response to the antigen in the subject, since Th2 responses provide efficient B cell help and promote IgG1 production. Alternatively, to promote a cellular immune response to an antigen of interest, the antigen and an inhibitory agent of the invention can be coadministered to a subject to promote a Th1 response to timmantigen in a subject, since Th1 responses favor the development of cell-mediated immune responses (e.g., delayed hypersensitivity responses). The antigen of interest and the modulatory agent can be formulated together into a single pharmaceutical composition or in separate compositions. In a preferred embodiment, the antigen of interest and the modulatory agent are administered simultaneously to the subject. Alternatively, in certain situations it may be desirable to administer the antigen first and then the modulatory agent or vice versa (for example, in the case of an antigen that naturally evokes a Th1 response, it may be beneficial to first administer the antigen alone to stimulate a Th1 response and then administer a stimulatory agent, alone or together with a boost of antigen, to shift the immune response to a Th2 response).

III. Diagnostic Assays

In another aspect, the invention features a method of diagnosing a subject for a disorder associated with aberrant hepatocyte growth and/or plasma cell differentiation and/or T cell subset activity comprising:

(a) detecting expression of XBP-1 in cells (e.g., hepatocytes, or precursors thereof, or plasma cells, or precursors thereof, or T cells, or precursors thereof) of a subject suspected of having a disorder associated with aberrant hepatocyte growth and/or plasma cell differentiation and/or T cell subset activity;

(b) comparing expression of XBP-1 in cells of said subject to a control that is not associated with aberrant hepatocyte growth and/or plasma cell differentiation and/or T cell subset activity; and (c) diagnosing the subject for a disorder based on a change in expression of XBP-1 in cells of the subject as compared to the control.

The "change in expression of XBP-1" in cells of the subject can be, for example, a change in the level of expression of XBP-1 in cells of the subject, which can be detected by assaying levels of XBP-1 mRNA, for example, by isolating cells from the subject and determining the level of XBP-1 mRNA expression in the cells by standard methods known in the art, including Northern blot analysis, reverse-transcriptase PCR analysis and in situ hybridizations. Alternatively, the level of expression of XBP-1 in cells of the subject can be detected by assaying levels of XBP-1 protein, for example, by isolating cells from the subject and determining the level of XBP-1 protein expression by standard methods known in the art, including Western blot analysis, immunoprecipitations, enzyme linked immunosorbent assays ELISAs) and immunofluorescence.

In another embodiment, a change in expression of XBP-1 in cells of the subject result from one or more mutations (i.e., alterations from wildtype) in the XBP-1 gene and mRNA leading to one or more mutations (i.e., alterations from wildtype) in the XBP-1 amino acid sequence of the XBP-1 protein. In one embodiment, the mutation(s) leads to a form of XBP-1 with increased activity (e.g., partial or complete constitutive activity), hi another embodiment, the mutation(s) leads to a form of XBP-1 with decreased activity (e.g., partial or complete inactivity). The mutation(s) may change the level of expression of XBP-1, for example, increasing or decreasing the level of expression of XBP-1 in a subject with a disorder. Alternatively, the mutation(s) may change the regulation of XBP-1, for example, by altering the interaction of the mutant XBP-1 with targets of XBP-1. Mutations in the nucleotide sequence or amino acid sequences of XBP-1 can be determined using standard techniques for analysis of DNA or protein sequences, for example for DNA or protein sequencing, RFLP analysis, and analysis of single nucleotide or amino acid polymorphisms.

In preferred embodiments, the diagnostic assay is conducted on a biological sample from the subject, such as a cell sample or a tissue section (for example, a freeze-dried or fresh frozen section of tissue removed from a subject), hi another embodiment, the level of expression of XBP-1 in cells of the subject can be detected in vivo, using an appropriate imaging method, such as using a radiolabeled anti-XBP-1 antibody.

In one embodiment, the level of expression of XBP-1 in cells of the test subject may be elevated (i.e., increased) relative to the control not associated with the disorder or the subject may express a constitutively active (partially or completely) form of XBP-1. This elevated expression level of XBP-1 or expression of a constitutively active form of XBP-1 can be used to diagnose a subject for a disorder associated with increased hepatocyte growth, such as hepatocellular carcinoma, or increased plasma cell differentiation, such as multiple myeloma or an autoimmune disease associated with pathogenic autoantibody production, or increased Th2 cell activity (as discussed above).

In another embodiment, the level of expression of XBP-1 in cells of the subject may reduced (i.e., decreased) relative to the control not associated with the disorder or the subject may express an inactive (partially or completely) mutant form of XBP-1. This reduced expression level of XBP-1 or expression of an inactive mutant form of XBP-1 can be used to diagnose a subject for a disorder associated with decreased hepatocyte growth, such as hepatic injury, hepatic disease (e.g., viral infection) or hepatic toxicity (e.g., cirrhosis) or decreased plasma cell differentiation, such as immunodeficiency disorders characterized by insufficient antibody production, or decreased Th2 cell activity and/or increased Th1 cell activity (as discussed above).

IV. Kits of the Invention

Another aspect of the invention pertains to kits for carrying out the screening assays, modulatory methods or diagnostic assays of the invention. For example, a kit for carrying out a screening assay of the invention can include an XBP-1-containing indicator composition, means for determining hepatocyte growth and/or plasma cell differentiation and/or T cell subset activity and instructions for using the kit to identify modulators of hepatocyte growth and/or plasma cell differentiation and/or T cell subset activity (e.g., Th2 cytokine production). In another embodiment, a kit for carrying out a screening assay of the invention can include XBP-1 deficient cells, means for determining hepatocyte growth and/or plasma cell differentiation and/or T cell subset activity (e.g., Th2 cytokine production) and instructions for using the kit to identify modulators of hepatocyte growth and/or plasma cell differentiation and/or T cell subset activity.

In another embodiment, the invention provides a kit for carrying out a modulatory method of the invention. The kit can include, for example, a modulatory agent of the invention (e.g., XBP-1 inhibitory or stimulatory agent) in a suitable carrier and packaged in a suitable container with instructions for use of the modulator to modulate hepatocyte growth and/or plasma cell differentiation and/or T cell subset activity.

Another aspect of the invention pertains to a kit for diagnosing a disorder associated with aberrant hepatocyte growth and/or plasma cell differentiation and/or T cell subset activity in a subject. The kit can include a reagent for determining expression of XBP-1 (e.g., a nucleic acid probe for detecting XBP-1 mRNA or an antibody for detection of XBP-1 protein), a control to which the results of the subject are compared, and instructions for using the kit for diagnostic purposes.

V. Cells, Embryos and Animals of the Invention

Another aspect of the invention pertains to isolated XBP-1 deficient cells, embryos and non-human animals that can be used in the various screening methods of the invention. Preferred XBP-1 deficient cells are hepatocytes, hepatocyte precursors, plasma cells, plasma cell precursors (B cells), T cells and T cell precursors. Preferred non-human animals, and embryos thereof, are mice. In one embodiment, the invention provides a homologous recombinant animal comprising a homozygous disruption of its endogenous XBP-1 gene, due to insertion of exogenous DNA into the gene, wherein this XBP-1 gene disruption prevents the expression of functional XBP-1 protein and, further, wherein the phenotype of this animal relative to an animal having a functional XBP-1 protein comprises decreased growth of hepatocytes or decreased differentiation of plasma cells or decrease production of Th2 cytokines. In another embodiment, the invention provides a homozygous XBP-1 deficient animal having a homozygous mutation inserted into its endogenous XBP-1 gene by homologous recombination in embryonic stem cells such that the XBP-1 gene of the animal is non-functional or does not express functional XBP-1 protein, and wherein the animal exhibits decreased hepatocyte growth or plasma cell differentiation or Th2 cytokine production. The construction and phenotypic characterization of preferred XBP-1 deficient non-human animals of the invention are described in detail in Example 1.

Since the XBP-1−/− phenotype leads to lethality in utero when the deficiency is constitutive, another preferred XBP-1 deficient animal is one in which expression of the XBP-1 deficient phenotype is controlled in a regulated manner, through "turning off of the XBP-1 gene in a controlled manner (e.g., through use of a controllable regulatory system, such as the tetracycline-regulated system). Accordingly, the invention further provides a transgenic non-human animal whose endogenous XBP-1 alleles have been altered, via exogenous DNA, such that expression of the endogenous XBP-1 alleles is regulated in a controlled manner by an inducing or suppressing agent, such that under at least certain conditions the XBP-1 alleles are non-functional or do not express a functional XBP-1 protein and wherein the animal exhibits decreased hepatocyte growth or plasma cell differentiation or Th2 cytokine production. Methods for constructing such "conditional" knockout animals are known in the art, such as, for example, a tetracycline-regulated system for conditional disruption of a gene as described in WO 94/29442 and U.S. Pat. No. 5,650,298.

Another preferred XBP-1 deficient animal is a chimeric animal (e.g., mice) produced using a blastocyst complementation system, such as the RAG-2 blastocyst complementation system, in which a particular organ or organs (e.g., the lymphoid organs) arise from embryonic stem (ES) cells with homozygous mutations of the XBP-1 gene. Accordingly, the invention provides a non-human chimeric animal in which at least one organ arises from embryonic stem cells with homozygous mutations of the XBP-1 gene. The construction and phenotypic characterization of preferred XBP-1 deficient chimeric non-human animals of the invention are described in detail in Example 2.

The XBP-1−/− animals of the invention further can be used to create transgenic animals carrying an XBP-1 transgene that allows for expression of the XBP-1 transgene in one or more specific cell types or tissues, such as hepatocytes. Such animals may be of particular use in "rescuing" the embryonic lethality of the XBP-1−/− animals (e.g., by allowing for expression of XBP-1 in developing hepatocytes) while still maintaining the XBP-1 deficiency in other cell types or tissues of the animal (such as the lymphoid system). A preferred transgenic animal is an XBP-1−/− knockout animal that carries an XBP-1 transgene controlled by the albumin promoter (a liver-specific regulatory element described in Pinkert et al. (1987) Genes Dev. 1:268-277). Alternatively, other liver-specific regulatory elements known in the art can be used to control expression of the transgene. Accordingly, the invention provides a non-human animal having a homozygous mutation inserted into its endogenous XBP-1 gene by homologous recombination in embryonic stem cells such that the endogenous XBP-1 gene of the animal is non-functional or does not express functional XBP-1 protein but wherein the non-human animal further comprises an XBP-1 transgene that directs expression of XBP-1 in at least one cell type or tissue type in the animal. Preferably, the transgene directs expression of XBP-1 in at least hepatocytes.

This invention is further illustrated by the following examples which should not be construed as limiting. The contents of all references, patents and published patent applications cited throughout this application are hereby incorporated by reference.

EXAMPLE 1

Production and Characterization of the Liver Phenotype of XBP-1 Deficient Mice

Disruption of the XBP-1 Gene

To define the actions of the XBP-1 protein in vivo, the XBP-1 gene was disrupted in embryonic stem cells by replacing a 0.8 kb fragment containing parts of exons 1 and 2 as well as the intervening intron with a neomycin resistance gene, resulting in a frame shift of the remaining amino acids (as diagrammed in FIG. 1). The targeting construct was generated by cloning the disrupted XBP-1 fragment into the vector pBS/TK, followed by linearization and introduction into D3 ES cells by electroporation. The cells were grown in neomycin and gancyclovir to achieve positive/negative selection, and resistant clones were tested for homologous integration of the disrupted XBP-1 fragment by performing Southern blots of genomic DNA One of three ES clones which had undergone targeted disruption of the XBP-1 gene transmitted the disrupted allele to offspring and XBP-1+/− mice were intercrossed to generate XBP −/− mice, as demonstrated by Southern blot analysis of genomic DNA from embryos. Northern blot analysis of total cellular RNA made from +/+ and −/− embryos revealed an absence of a correctly-sized XBP-1 transcript in −/− samples and the appearance of a fainter, higher MW transcript, which also hybridized with a neomycin cDNA probe. Western blot analysis of extracts from XBP-1+/+, +/−, and −/− fetal livers using a monoclonal antiserum specific for XBP-1 revealed an absence of immunoreactive XBP-1 protein in the −/− samples.

Embryonic Lethality from Liver Hypoplasia in XBP-1-/- Mice

Matings of heterozygous XBP-1 mice produced no -/- live births. Of over 400 pups born no homozygotes were obtained, suggesting that XBP-1 is necessary for survival. Genotyping of litters harvested from serial timed matings revealed embryonic lethality beginning at E12.5. By E13.5, XBP-1-/- embryos could be recognized by their growth retardation, pale coloration, and hypoplastic livers. Inspection of -/- livers showed them to be markedly reduced in size compared to normal E13.5 livers, and total liver cell counts were 15% of +/+ livers at this age. Histologic analysis of -/- E14.5 livers revealed reduced cellularity and increased empty space indicating less dense packing of cells in the -/- as compared to the control livers.

Since the fetal liver becomes the main hematopoietic organ by E 13.5, fetal blood counts were determined to assess whether severe liver hypoplasia correlated with abnormal red blood cell production. Anemia became evident in XBP-1-/- embryos after E11.5 as hematopoiesis switched from the yolk sac to the fetal liver. By E 14.5, the total blood counts of surviving XBP-1-/- mice were 20% of the values found in normal littermates. Cytospin preparations of peripheral blood at E 13.5 revealed that -/- erythroid cells were predominantly immature, nucleated cells of yolk sac origin, while +/+ erythroid cells were 80% liver-derived nonnucleated cells. Cytospin preparations of E 13.5 liver cells demonstrated the presence of erythroid and myeloid lineage cells at all stages of maturity in -/- specimens, though in reduced numbers consistent with the hypoplastic livers.

To compare the potential of +/+ and -/- hematopoietic progenitor cells to develop into the erythroid and myeloid lineages, in vitro methylcellulose colony assays were performed using fetal AGM (aorto-gonad mesonephros), yolk sac, or liver as the source of progenitor cells (Muller et al. 1994, *Immunity* 1:291-301; Wang et al. 1997, *EMBO J.*, 16:4374-4383). The cultures were performed as described in Wang et al. with cultures using erythropoietin alone or erythropoietin, IL-1, IL-3, and G-CSF. All three of the tissues (fetal AGM, yolk sac and liver) gave rise to equivalent numbers of erythroid and myeloid colonies from +/+ and -/- samples, indicating that pluripotent hematopoietic stem cells are found in all three locations. Although -/- fetal livers are severely hypoplastic, some hematopoietic stem cells do migrate there and have the potential to give rise to all hematopoietic lineages, as also seen in cytospin preparations of fetal liver. Since the XBP-1-/- hematopoietic committed progenitor cells were able to proliferate and differentiate normally when tested in vitro, the anemia seen in these embryos cannot be attributed to a hematopoietic cell-autonomous defect. These findings were reinforced by an analysis of chimeric mice derived from XBP-1-deficient embryonic stem cells in the RAG-2-deficient complementation system (described further in Example 2). In these animals, the livers were almost exclusively of RAG-2-deficient cell origin, while reconstitution of hematopoietic elements such as B- and T-lymphocytes from XBP-1-deficient precursors occurred. Therefore, although XBP-1-deficient embryonic stem cells do not contribute to normal liver development, they are not defective in the reconstitution of hematopoietic elements.

XBP-1 Expression in the Developing Liver of Wild Type Mice

The fetal liver begins its development as an outpouching of foregut endoderm (Gualdi et al. 1996, *Genes Dev.* 10:1670-1682). At E10.5, the liver bud of wild-type mice was found to express high levels of XBP-1 mRNA by in situ hybridization. For in situ hybridization, wild-type embryos were sectioned and probed for XBP-1 as described (Clauss etal 1993, *Dev. Dynamics* 197:146-156'). As E10.5 represents a time point before significant population of the liver by hematopoietic cells, it demonstrates that XBP-1 is expressed in hepatic parenchymal cells. Northern blotting of RNA also showed high levels of XBP-1 mRNA in hepatic stromal cell lines and in HepG2 hepatocarcinoma cells. This evidence further supports a role for XBP-1 in liver growth rather than in hematopoietic cell division and differentiation.

Reduced Growth Rate and Increased Apoptosis in XBP-1-deficient Livers

Two mechanisms that account for the severely hypoplastic livers in XBP-1 embryos were identified: reduced growth rate and increased apoptosis. To directly demonstrate reduced cell growth, mice at day 13.5 of pregnancy were injected with BrdU, and the fetuses were harvested and analyzed for BrdU incorporation. Pregnant mice were injected IV with 0.3 ml of 50 mg/ml BrdU (Sigma) in PBS. Embryos were harvested after 1 hour and fixed in Carney's fixative. After embedding in paraffin, detection of BrdU was performed following the instructions of the BrdU labeling kit (Roche). Wild-type fetal livers showed heavy nuclear staining in the entire liver, while XBP-1-deficient samples had less staining with significant areas remaining unstained, especially towards the center of the liver. The reduced BrdU incorporation in XBP-1-/- livers directly demonstrates a subnormal rate of growth in this organ.

Apoptosis was identified morphologically and by TUNEL staining of E13.5 fetal livers. The TUNEL assay was performed using the Cell Death Kit (Roche). These experiments showed a markedly elevated rate of apoptotic hepatocytes in XBP-1-/- samples. In contrast, the apoptotic cells identified in +/+ were generally of the myeloid lineage. Staining with chloroacetate esterase was used to confirm that hepatocytes, and not myeloid lineage cells, accounted for most of the apoptotic cells in -/- liver samples.

XBP-1 Induction After Partial Hepatectomy

To further study the role of XBP-1 in liver growth and gene induction, partial hepatectomies were performed on normal adult mice. In this model, the remnant liver reverts to a quasi-fetal phenotype and undergoes rapid cell division to reestablish the original weight of the organ within 10 days (Michalopoulos and DeFrances 1997, *Science* 276:60-66). Among the first steps in this process is the activation of pre-formed transcription factors such as NF-/cB or STATS (Taub 1996, *FASEB J.* 10:413-427). These factors then induce transcription of immediate early genes, many of which encode transcription factors such as AP-1, NF-/cB, and certain CREB/ATF family members such as CREB and CREM (Servillo et al. 1998, *Genes Dev.* 12:3639-3643; Taub 1996, *FASEB J.* 10:413-427).

The left and caudate lobes of the liver were removed from wild-type adult mice. Remaining liver tissue was harvested in a time course for total RNA isolatioa Northern blots were probed with cDNA for XBP-1, C/EBPP, and the control gene P2M. Results of partial hepatectomies in mice now demonstrate that XBP-1 is an immediate early gene in this process, induced within 30 minutes of surgery but having a prolonged peak of induction past 16 hours. This time course is similar to the induction of C/EBPp, which peaks slightly earlier at 14 hours post hepatectomy. It is expected that XBP-1 acts as a homodimer or heterodimer to bind at CRE-like sites and in turn upregulates the delayed-early genes involved in liver regeneration. The decreased liver cell proliferation seen in XBP-1–/– embryos indicates that XBP-1, like CREB and CREM, is a CRE-binding transcription factor involved in hepatic proliferation.

Identification of XBP-1 Target Genes in Liver

To identify target genes for XBP-1 action in the liver, differential hybridization to microarray chips was compared in samples derived from E13.5+/+ or –/– livers. RNA was isolated from +/+ and –/– E13.5 livers by lysis in guanidine and centrifugation through a CsCl cushion. Ten ug of total RNA were converted to double-stranded cDNA using an oligo dT primer with a T7 RNA polymerase site on its 5' end (5'-GGCCAGTGAATTGTAATACGAC TCACTATAGG-GAGGCGG-3[1]) (SEQ ID NO: 1). The cDNA was used directly in an in vitro transcription reaction in the presence of biotinylated nucleotides Bio-11-UTP and Bio-11-CTP (Enzo, Farmingdale, N.Y.). To improve hybridization kinetics, the labeled antisense RNA was fragmented by incubating at 94° C. for 35 min in 30 mM MgOAc, 100 mM KOAc. Hybridization to Genechips™ (Affymetrix, San Jose, Calif.) displaying probes for 250 genes of immunological interest or 250 genes with roles in development was done at 40° C. overnight in a mix including 10 jag fragmented RNA, 6×SSPE, 0.005% Triton-X-100, and 100 mg/ml herring sperm DNA in a total volume of 200 jil. Chips were washed, stained with phycoerythrin-streptavidin, and read using an Affymetrix GeneChip scanner and accompanying gene expression software. The software includes algorithms that determine whether a gene is absent or present and whether the expression level of a gene in the –/– sample was significantly increased or decreased relative to the +/+ sample.

The genes for ctl-antitrypsin and a-fetoprotein were found to be expressed at significantly reduced levels in –/– samples, as also shown in Northern blots of +/+ and –/– fetal liver mRNA Both gene products are acute phase proteins synthesized by hepatocytes and are expressed during development as well as in adult liver. Two other acute phase proteins, transthyretin and apolipoprotein A1 were also found to have decreased levels of mRNA in –/– livers, while multiple other acute phase proteins and hepatocyte-expressed genes (vitamin D binding protein, C-reactive protein, serum amyloid P, al-acid glycoprotein, hepatocyte growth factor) were expressed equally in +/+ and –/– samples. This indicates that XBP-1-deficient hepatocytes have defects in the synthesis of specific gene products rather than a global reduction in transcription.

To demonstrate direct regulation of the al-antitrypsin promoter by XBP-1, transient transfections were performed using an XBP-1 expression plasmid and al-antitrypsin luciferase reporter constructs in the HepG2 cell line. Although this cell line contains endogenous XBP-1, overexpression of XBP-1 could transactivate the al-antitrypsin promoter by 3.5 fold. As controls for specificity of the XBP-1 effect, the use of a frameshifted XBP-1 expression construct or the mutation of an XBP-1 target site in the al-antitrypsin promoter eliminated all transactivation. Transactivation of an a-fetoprotein reporter construct by the XBP-1 expression plasmid was also demonstrated in vitro. Therefore, XBP-1 has a specific transcriptional effect on these two acute phase protein genes.

The phenotype of XBP-1-deficient embryos shows similarities to several mouse models in which gene disruptions result in abnormal liver development. Disruption of the homeobox gene Hlx resulted in initial liver specification but only minimal growth and represents an earlier, more severe defect than XBP-1 deficiency (Hentsch et al. 1996, *Genes Dev.* 10:70-79). Abnormal liver growth has been described in HGF/SF-deficient embryos with a phenotype similar to the XBP-1–/– embryos: loosened liver structure, enlarged sinusoidal spaces, and dissociation of parenchymal cells (Schmidt et al. 1995, *Nature* 373:699-702; Uehara et al. 1995, *Nature* 373:702-705). However, HGF mRNA levels are normal in XBP-1–/– embryos. MTF-1 deficiency resulted in a dissociated hepatic epithelial compartment, enlarged sinusoids, but unlike XBP-1–/– embryos, no significant decrease in liver size and no anemia (Gunes et al. 1998, *EMBO J.* 17:2846-2854). Deficiency in c-jun also led to hypoplasia and dissociation of liver cells and death by E15.5, but c-jun mRNA levels were normal in XBP-1–/– embryos. A small liver can be the result of abnormal hematopoietic cell proliferation, as described in c-myb-deficient embryos (Mucenski et al. 1991, *Cell* 65:677-689), or abnormal erytiroid cell proliferation and differentiation, as seen in Rb –/– embryos (Lee et al. 1992, *Nature* 359: 288-294; Jacks et al. 1992, *Nature* 359:295-300). hi contrast, we found normal in vitro proliferative and differentiative function of XBP-1–/– hematopoietic progenitor cells. The homing of hematopoietic cells to the liver was the presumed defect in the absence of 01 integrin (Hirsch et al. 1996, *Nature* 380:171-175; Faessler et al. 1995, *Genes Dev.* 9:1896-1908), but XBP-1–/– livers showed normal hematopoietic potential on aper-cell basis. Finally, apoptosis has contributed to the liver failure in Rb –/–, RelA –/– (Beg et al. 1995, *Nature* 376:167-170), and HGF/SF –/– embryos (Schmidt et al. 1995, *Nature* 373:699-702; Uehara et al. 1995, *Nature* 373:702-705), as was also seen in XBP-1–/– embryos. XBP-1 is not known to act directly upstream of these multiple factors that are important in normal hepatogenesis but instead contributes a unique function to liver growth and development. It is possible that XBP-1–/– hepatic parenchymal cells may be defective in their ability to support proliferation of hematopoietic progenitor cells. Analysis of mRNA has not identified altered levels of (31 integrin, HGF, c-myb, c-kit ligand, AML-1, Rb, or c-jun in XBP-1–/– embryos, making these genes unlikely to be major targets of regulation by XBP-1 during liver development.

Instead, our data have identified four acute phase protein genes expressed in hepatocytes during liver growth as specific targets of XBP-1. The induction of acute phase proteins represents liver-specific gene activation, whether during embryonic development or in adults after injury from partial hepatectomy, inflammation, infection, toxins, or malignancy. The systemic role of some acute phase proteins has been defined in detail, such as the serum protease inhibition by al-antitrypsin or the antiatherogenic properties of apolipoprotein-A1 (Andersson 1997, *Curr. Opin. Lipidol.* 8:225-228; Gabay and Kushner 1999, *New Engl. J. Med.* 340:448-454). A reduction in the levels of these acute phase proteins reflects a decrease in specific hepatocyte protein synthesis, but individually, deficiency of these genes is not known to result in the defects observed in XBP-1-deficient livers. The XBP-1-regulated acute phase protein AFP is highly expressed in fetal liver and yolk sac and represents one of the earliest phenotypic markers of the fetal liver (Gualdi et al. 1996, *Genes Dev.* 10: 1670-1682). It has been speculated that a major function of AFP is to promote cell growth in the liver, possibly by sequestering estrogen, which otherwise has antiproliferative effects (reviewed by Chen et al. 1997, *Crit. Rev. Euk. Gene. Exp.* 7:11-41). AFP levels are very low in adult liver but rise upon liver regeneration and in the majority of hepatocellular carcinomas. Indeed, AFP was among the first tumor markers to be recognized. We have demonstrated that in the absence of XBP-1, AFP is expressed only at reduced levels, and that liver growth is severely impaired. Our data establish that XBP-1 is involved in the growth and survival of hepatocytes, and through its regulation of acute phase protein genes, also in the expression of liver-specific genes. These studies have demonstrated that XBP-1 directly controls a subset of the liver's protein synthetic activity, and that normal liver growth cannot be achieved in the absence of XBP-1 protein.

EXAMPLE!

Characterization of the Plasma Cell Phenotype of XBP-1 Deficient Mice

Generation of XBP-1-deficient/RAG-2-deficientchimeric Mice

XBP-1 deficiency causes death from anemia and liver hypoplasia in utero (see Example 1). Therefore, studies of immune function in the setting of XBP-1 deficiency were performed in the RAG-2 complementation system. First, embryonic stem cells with one XBP-1 allele previously disrupted by a Neomycin cassette had their second XBP-1 allele disrupted by homologous recombination. The construct deleted parts of exons 1 and 2, as well as the intervening intron, and substituted a Hygromycin resistance sequence. ES cells with one allele of XBP-1 previously disrupted by the Neomycin gene were transfected with the new construct and selected in Hygromycin, Neomycin and gancyclovir. Surviving clones were screened by Southern blotting for the presence of 2 disrupted XBP-1 alleles and loss of the wild-type allele. Appropriate ES clones were injected into RAG-2-deficient blastocysts and implanted into pseudopregnant female mice by standard methods. The resulting mice were assayed for lymphoid reconstitution by FACS analysis of peripheral blood mononuclear cells using anti-CD3 and anti-B220 antibodies.

After injection into RAG-2-deficient blastocysts, XBP-1-deficient cells contributed to reconstitution of peripheral blood B- and T-lymphocytes in about half the mice born. In these reconstituted animals, XBP-1-deficient ES cells contributed heavily to lymphoid organs, variably to heart, lung, kidney and muscles, but minimally to liver, consistent with the essential role of XBP-1 in hepatocyte development seen in XBP-1-/- embryos.

The reconstitution of lymph nodes and spleen in XBP-1/RAG-2-/- animals resulted in normal numbers and percentages of B- and T-lymphocytes in most of the chimeric animals compared to wild-type 129 control mice, in addition, B lymphocytes from wild-type and XBP-1/RAG-2 mice had indistinguishable patters of cell surface staining for IgM, IgD and B220.

Deficient Serum Immunoglobulin Production by XBP-1-/- B Cells

To assess a major function of B lymphocytes, immunoglobulin levels were assayed by ELISA in the serum of XBP-1 /RAG-2-/- mice and control 129 Sv/LtnJ mice. All animals were housed under specific pathogen-free conditions. ELISA assays of immunoglobulin levels in serum were performed using standard techniques. The finding were that XBP-1/RAG-2-/- animals had a profound decrease in serum immunoglobulin levels for all Ig subtypes tested, with a small amount of IgG2a detected in some of the mice. To test the potential of XBP-1-deficient B cells for Ig production after in vitro stimulation, splenocytes or purified B cells (B220+ magnetic bead selection, Miltenyi Biotech) were plated at $1 \times 10^6$ cells/ml and stimulated with anti-CD40 antibody (1 ug/ml), anti-CD40 plus IL-4 (10 ng/ml), LPS (20 Mg/ml), or LPS plus IL-4 for four days. When immunoglobulin levels were determined on the culture supernatants (by ELISA, using standard methods), all tested Ig subtypes were again found at lower levels in the XBP-1-/- samples compared to control samples. Finally, antigen-specific production of immunoglobulin was assessed after immunization of mice with DNP-albumin, B cell harvest, and in vitro stimulation of B cells with DNP-KLH. Antigen-specific immunoglobulin production by XBP-1-/- B cells was severely decreased in this assay. The findings indicate that although XBP-1-deficient B cells can be generate in normal numbers, they are defective in becoming antibody-secreting plasma cells.

In vitro Phenotype of XBP-1-deficient B Cells

Having identified normal B cell numbers in spleen and lymph nodes yet functionally defective B cell terminal differentiation in XBP-1/RAG-2-/- mice, the phenotype of B cell activation was investigated in vitro. B cells were stimulated in vitro with anti-CD40 antibody (1 ug/ml), anti-CD40 plus IL-4 (10 ng/ml), LPS (20 ug/ml), or LPS plus IL-4 for up to four days. Cell proliferation was the same in XBP-1-deficient and control samples, as judged by equivalent cell counts on days 1 and 4 after culture. In addition, the B cell populations were activated similarly, as judged by analysis of the cell-surface activation markers MHC Class 11 and CD69. The in vitro stimuli were also designed to induce class switch recombination in B cells, e.g., switching to IgG2a and IgE by IL-4, and switching to IgG by anti-CD40 alone. Class switch recombination was equivalent in XBP1-/- and control samples, as judged by FACS analysis of cell surface immunoglobulin and by levels of recombined Ig mRNA.

The cytokine profile of in vitro cultured B cells was also studied. IL-6 production by XBP-1-/- B cells showed a mean decrease of 51%, compared to wild type B cells, following LPS stimulation (50 ug/ml) and 46%, compared to wild type B cells, following stimulation with LPS and IL-4 (10 ng/ml). However, no decrease in IL-6 production was observed following treatment with anti-CD40 (10 ug/ml) or anti-CD40 plus IL-4. Furthermore, in two experiments, production of IL-10 by XBP-1-/- B cells was the same as by wild type cells regardless of the stimulus (LPS, LPS+IL-4, anti-CD40 or anti-CD40+IL-4). Therefore, XBP-1-deficient B cells are present in normal numbers and can be activated in vitro to undergo proliferation, cell surface activation marker expression, class switch recombination, and cytokine secretion at near normal levels. Therefore, other mechanisms must account for the impaired immunoglobulin production by XBP-1-/- B cells.

Diminished Plasma Cell Generation in the Absence of XBP-1

To assess whether XBP-1-deficient B cells respond to activating stimuli in vivo, mice were immunized with DNP-albumin and draining lymph nodes were harvested after 9 days. Histologic analysis demonstrated normal germinal center formation in XBP-1/RAG-2-/- animals. This indicates that many of the B cell functions assayed in vitro, such as cell proliferation, activation, and class switch recombination, were also intact in vivo.

However, the generation of plasma cells was severely impaired in XBP-1/RAG-2-animals. Sections ofjejunum of XBP-1/RAG-2-/- versus control mice showed 70-fold more plasma cells in the controls. In addition, it was noted that the rare plasma cells seen in XBP-1/RAG-2-/- animals generally lacked the perinuclear halo, indicating that these cells did not have a large Golgi apparatus and were likely not secreting large amounts of immunoglobulins.

A further test of plasma cell generation was an assay for Syndecan-1-positive cells in DNP-albumin-immunized mice. Syndecan-1 is a cell surface glycoprotein upregulated on terminally differentiated plasma cells but absent on mature B cells. As predicted by the low level of immunoglobulin production, XBP-1-/- samples did not lead to the production of significant amounts of Syndecan-1 positive cells, while they were readily detected in the wild-type control. In addition, cultures of in vitro stimulated XBP-1-/- B cells were not only found to secrete less immunoglobulin than controls, but were also less differentiated as assayed by molecular techniques. Northern blots of mRNA from wild-type and XBP-1-/- B cells stimulated for 4 days in vitro were probed for expression of J chain, which is required for IgM and IgA assembly in plasma cells, as well as for c-myc, which becomes down-regulated as B cells exit the cell cycle to differentiate terminally. Total RNA was isolated using TriZol (Gibco) as recommended by the manufacturer. XBP-1-/- B cells had a less mature phenotype than control B cells, showing lower amounts of J chain mRNA and higher levels of c-myc mRNA Therefore, XBP-1/RAG-2-/- animals display a severe defect in their numbers of terminally differentiated plasma cells.

XBP-1 Expression in Plasma Cells in Rheumatoid Synovium

XBP-1 is ubiquitously expressed in adult tissues and previous work has shown that two of four plasma cell lines tested had extremely high levels of XBP-1 mRNA The disease rheumatoid arthritis offered a source of clinical material to study XBP-1 expression in a condition characterized by inflammatory cell infiltrates and rheumatoid factor production by plasma cells. Using in situ hybridization (which was performed using XBP-1-specific probes from the 5' and 3' untranslated portions of the cDNA), an antisense probe for XBP-1 showed strong hybridization to plasma cells in rheumatoid synovium, while a sense probe showed no specific hybridization. Serial sections histologically confirmed the identification of the plasma cells. This example shows the high-level expression of XBP-1 in the plasma cell infiltrate of an inflammatory disease.

XBP-1 Drives B Cell Differentiation

The finding of very few plasma cells in XBP-1/RAG-2-/- mice despite apparently normal germinal centers locates the primary site of XBP-1 action to the interval between full B cell activation and terminal differentiation. The BCLI-3B3 cell line is a highly activated B cell line that can be driven to an early plasma cell stage by IL-2 plus IL-5 treatment. The BCLI-3B3 cell line was obtained from the American Type Culture Collection and grown according to the supplied protocol. An expression construct containing XBP-1 and green fluourescent protein (GFP) was transfected into this cell line to study its ability to affect the stage of differentiation. Transfection was by electroporation at 290V, 275 fif in a BioRad electroporator. By FACS analysis, cells overexpressing XBP-1 but not the GFP vector alone showed signs of further maturation: a decrease in CD44 levels and the emergence of Syndecan-1 positive cells. Interestingly, an identical effect has been described for the transfection of the transcription factor Blimp-1 into BCL1-3B3 cells. However, Northern blots of activated B cells from normal and XBP-1/RAG-2-/- sources showed no difference in Blimp-1 mRNA levels. Therefore, XBP-1 acts downstream of Blimp-1 or via a separate pathway in its regulation of B cell differentiation.

A second action of overexpressed Blimp-1 is to cause apoptosis of B cells that are immature or not fully activated. To examine whether overexpression of XBP-1 could cause apoptosis of B cells, an XBP-1 expression construct was transfected into the Ball? mature B cell line. A similar finding to that observed with Blimp-1 was demonstrated in the Ball? line after transfection of increasing amounts of XBP-1 expression construct. Transfection of Ball? was by electroporation at 290V, 275/iF in a BioRad electroporator. The Ball? cell line was grown in RPMI medium with 10% fetal calf serum, 2 mM glutamine, 50 IU/ml penecillin, 50 ug/ml streptomycin, 100 ul beta-mercaptoethanol. Up to 12% apoptosis was seen when the highest amounts of XBP-1 were added.

EXAMPLE 3

Preparation of Anti-XBP-1 Monoclonal Antibodies

To prepare monoclonal antibodies against XBP-1, the XBP-1 cDNA encoding positions 226-884 was cloned into the vector pQR9, which encodes a histidine tag that is fused in frame to the XBP-1 coding sequences upon introduction of the cDNA into the vector. The His-tagged XBP-1 protein was expressed and used to immunize mice and monoclonal antibodies were made from lymphocytes of the immunized mice by standard techniques.

EXAMPLE 4

Characterization of the T Helper Cell Phenotype of XBP-1 Deficient Mice

Figure 2:
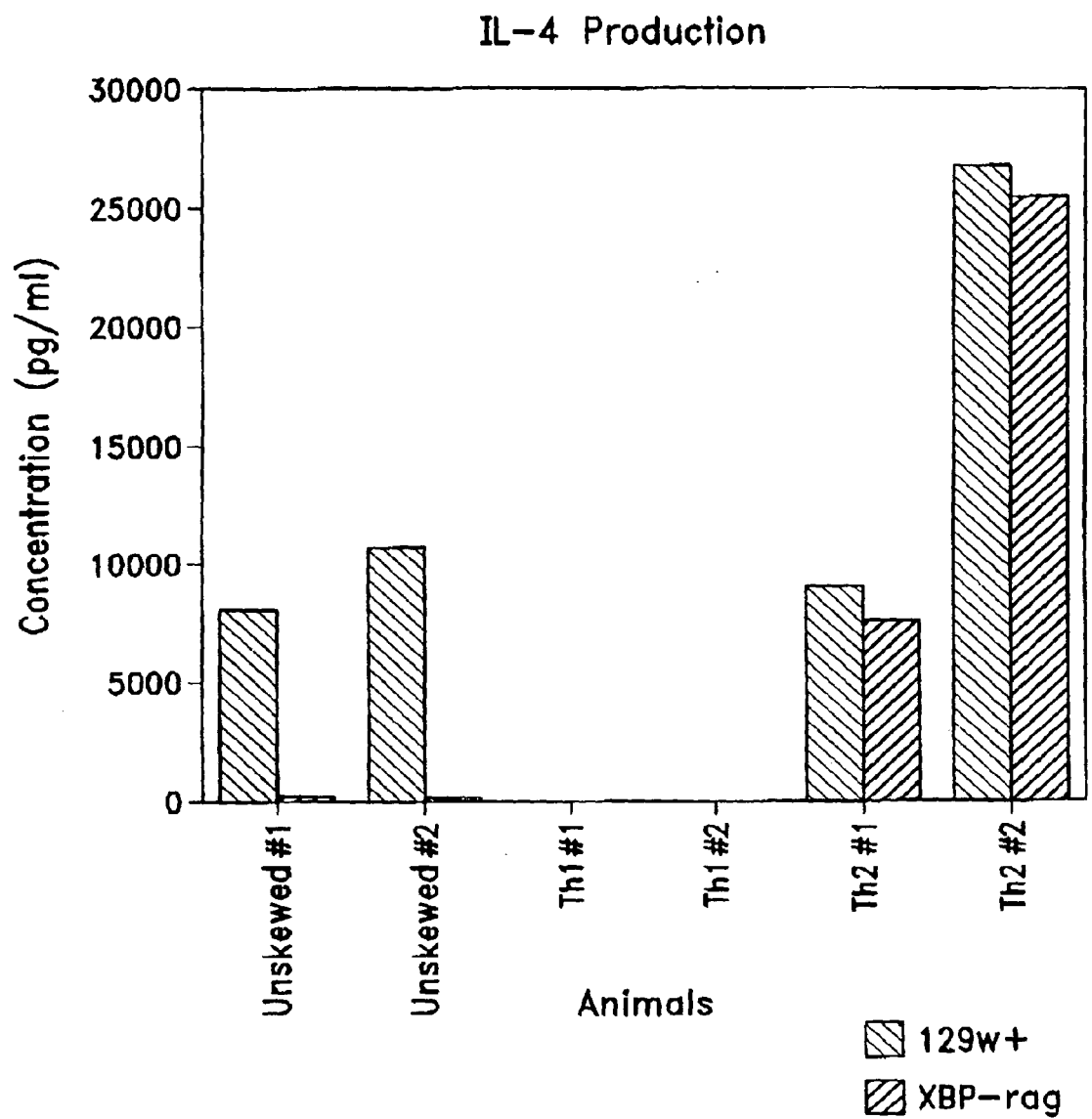
FIG. 2 is a bar graph illustrating IL-4 production by T cell populations from either control 129 wild type mice (129w+; dotted bars) or XBP-1-deficient/RAG-2-deficient mice (XBP-rag; shaded bars), wherein the T cells were cultured under conditions favoring either a Th1 phenotype ("Th1") or a Th2 phenotype ("Th2") or not favoring either ("Unskewed"). Results shown are from two different sets of animals.
Figure 3:
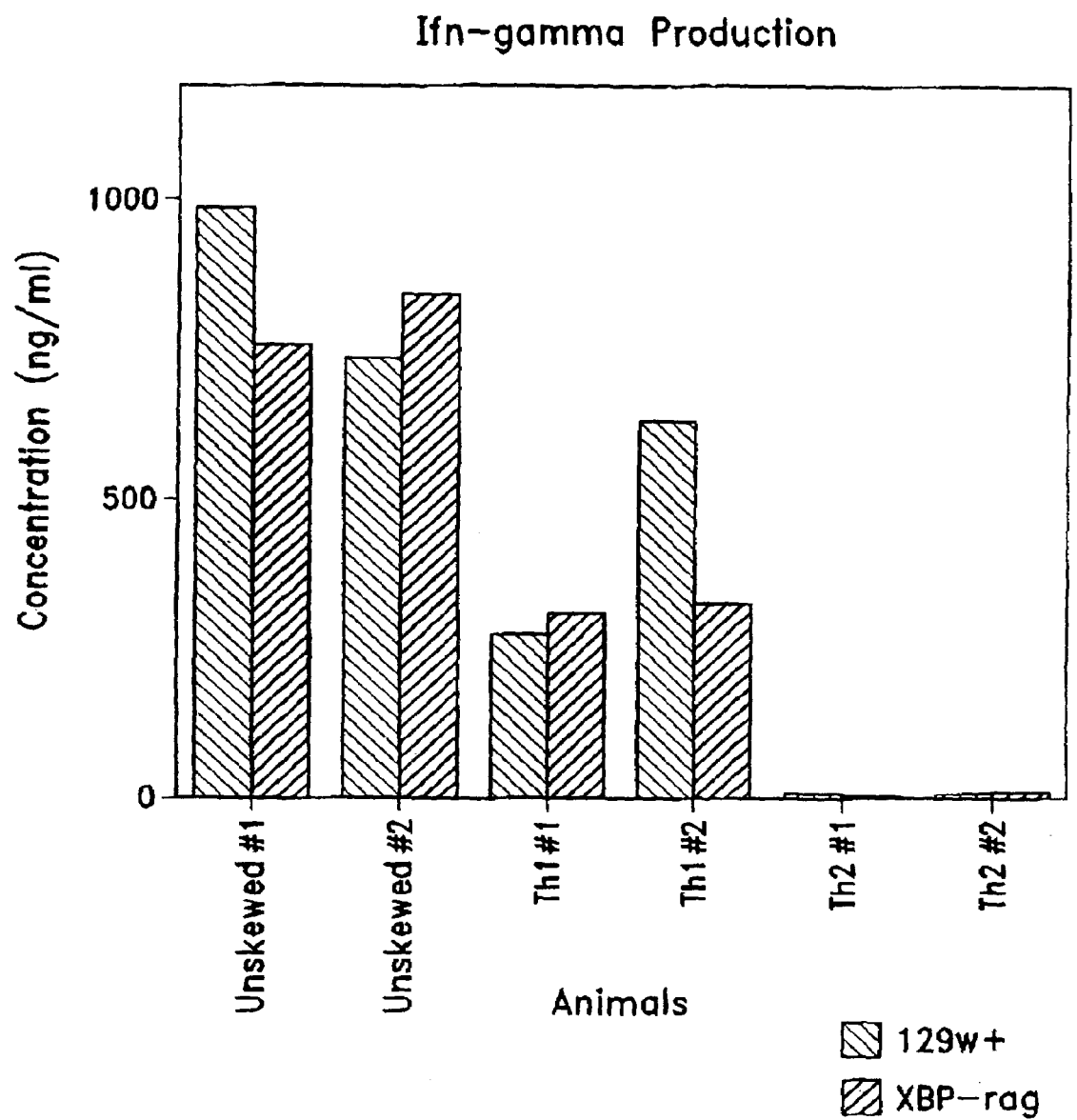
FIG. 3 is a bar graph illustrating interferon-gamma (IFN-y) production by T cell populations from either control 129 wild type mice (129w+; dotted bars) or XBP-1-deficient/RAG-2-deficient mice (XBP-rag; shaded bars), wherein the T cells were cultured under conditions favoring either a Th1 phenotype ("Th1") or a Th2 phenotype ("Th2") or not favoring either ("Unskewed"). Results shown are from two different sets of animals.
Figure 4:
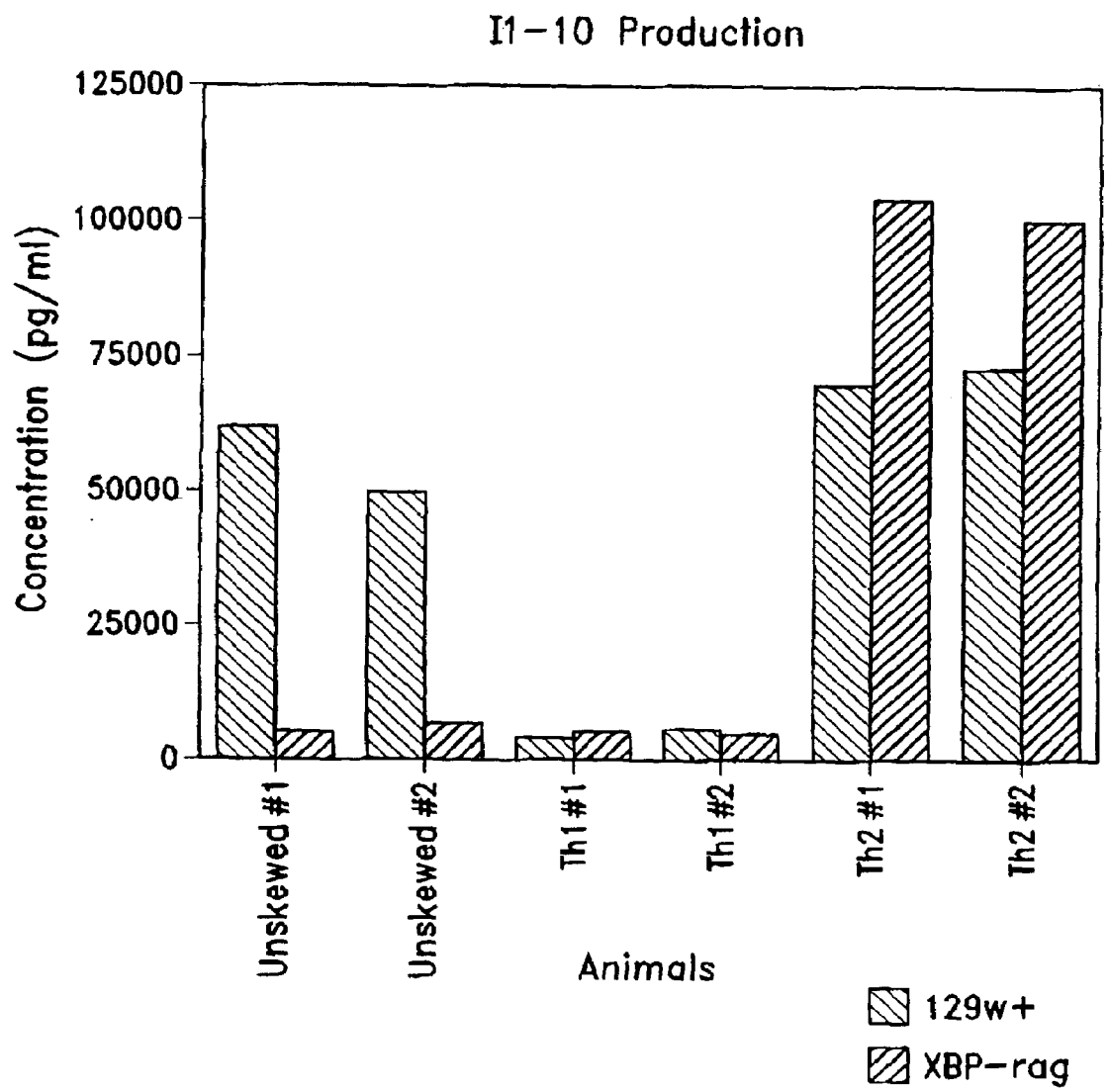
FIG. 4 is a bar graph illustrating IL-10 production by T cell populations from either control 129 wild type mice (129w+; dotted bars) or XBP-1-deficient/RAG-2-deficient mice (XBP-rag; shaded bars), wherein the T cells were cultured under conditions favoring either a Th1 phenotype ("Th1") or a Th2 phenotype ("Th2") or not favoring either ("Unskewed"). Results shown are from two different sets of animals.
Figure 5:
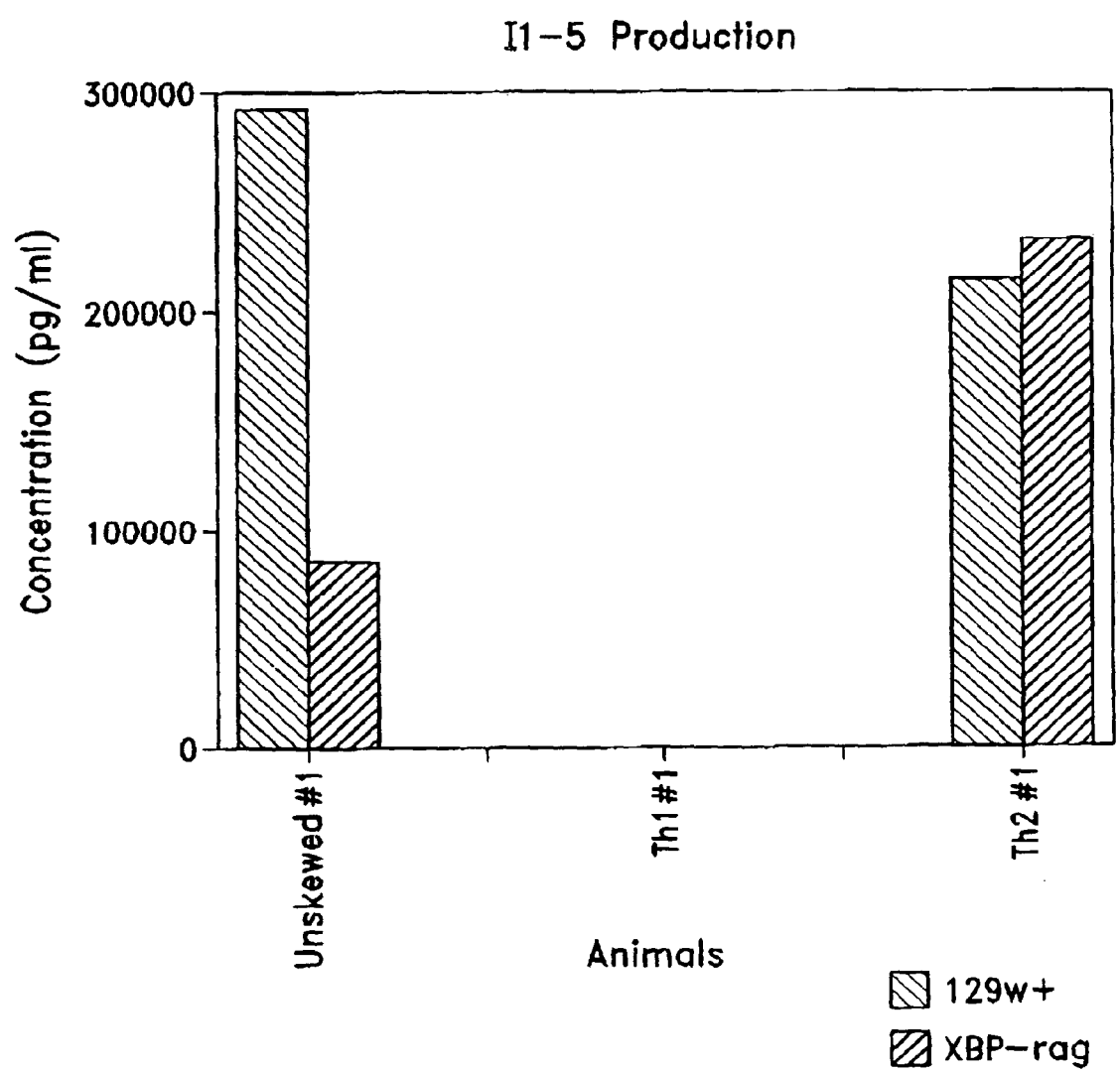
FIG. 5 is a bar graph illustrating IL-5 production by T cell populations from either control 129 wild type mice (129w+; dotted bars) or XBP-1-deficient/RAG-2-deficient mice (XBP-rag; shaded bars), wherein the T cells were cultured under conditions favoring either a Th1 phenotype ("Th1") or a Th2 phenotype ("Th2") or not favoring either ("Unskewed").
Figure 6:
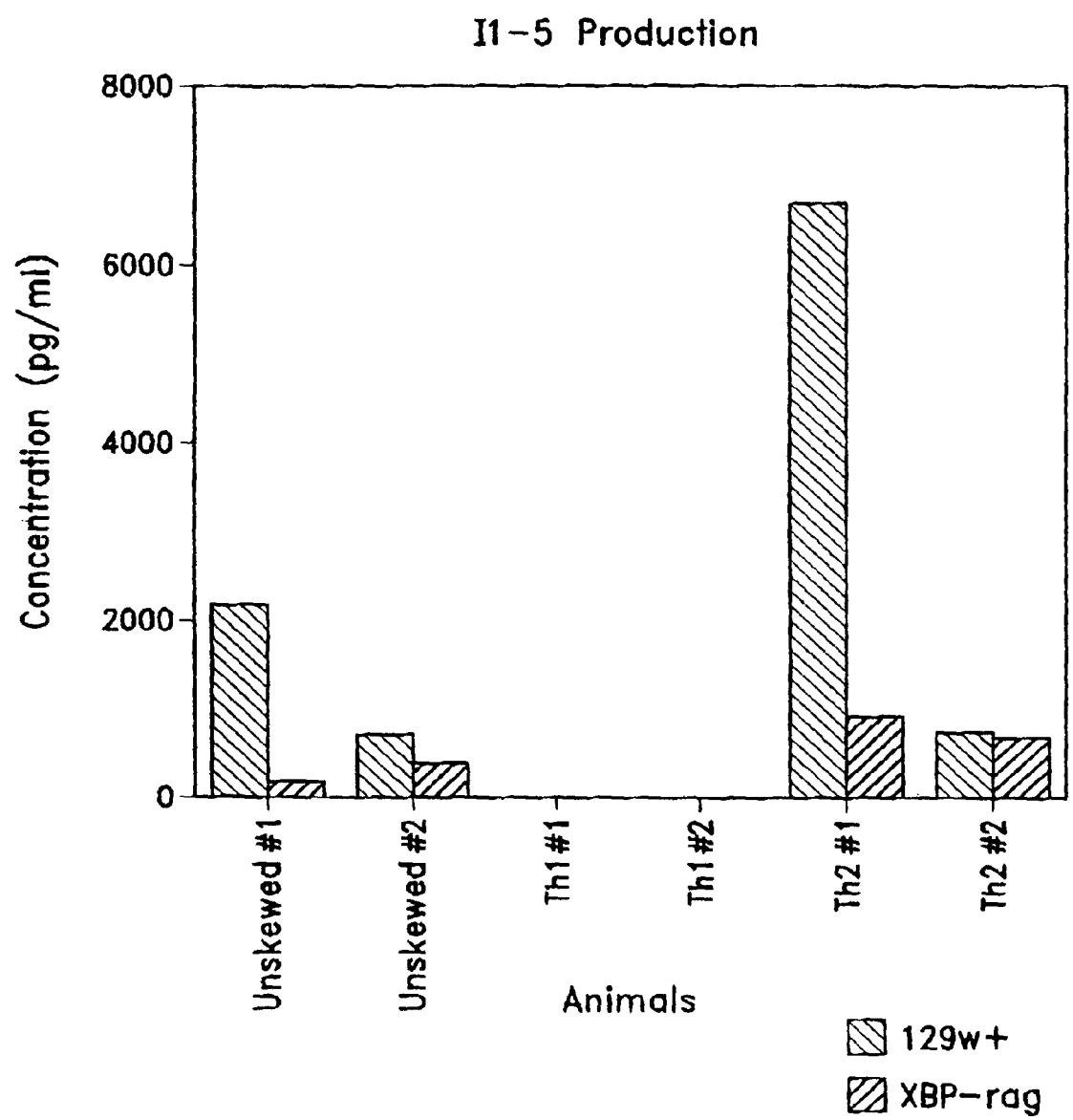
FIG. 6 is a bar graph illustrating IL-6 production by T cell populations from either control 129 wild type mice (129w+; dotted bars) or XBP-1-deficient/RAG-2-deficient mice (XBP-rag; shaded bars), wherein the T cells were cultured under conditions favoring either a Th1 phenotype ("Th1") or a Th2 phenotype ("Th2") or not favoring either ("Unskewed"). Results shown are from two different sets of animals.

Cytokine production by T cells of XBP-1-deficient/RAG-2-deficient chimeric mice was studied to examine the effect of XBP-1 deficiency on T helper cell subsets. T cells were isolated from XBP-1-deficient/RAG-2-deficient mice (XBP-rag) and from strain 129 wild type mice (129w+) as controls. The cells were cultured in vitro under conditions that favored either Th1 differentiation or Th2 differentiation, or that didn't favor development of either type of helper cell (unskewed conditions). To induce Th1 differentiation, cells were cultured with 5 ng/ml recombinant IL-12 and 10 ug/ml anti-IL-4 antibody. To induce Th2 differentiation, cells were cultured with 10 ng/ml recombinant IL-4, 10 ug/ml anti-IFN-y antibody and 10 ug/ml anti-IL-12 antibody. Production of the following cytokines by the different cell populations was measured by ELISA: IL-4, IFN-y, IL-10, IL-5 and IL-6. Bar graphs illustrating the results from two different sets of animals are shown in FIG. 2 (IL-4), FIG. 3 (IFN-Y), FIG. 4 (IL-10), FIG. 5 (IL-5) and FIG. 6 (IL-6).

The results demonstrate that for the Th2 type cytokines examined (IL-4, IL-10, IL-5 and IL-6), T cells from the XBP-1-deficient mice displayed a defect in the ability to produce these cytokines when the cells were cultured under unskewed conditions (see FIGS. 2, 4, 5 and 6, columns at left). In contrast, T cells from XBP-1-deficient mice still retained the ability produce the Th1 type cytokine IFN-y when cultured under unskewed conditions (see FIG. 3, columns at left), as well as under conditions that favored Th1 cell development (see FIG. 3, middle columns). The defect in Th2 cytokine production by the XBP-1 deficient T cells was overcome by culturing the T cells under conditions favoring Th2 cell development (see FIGS. 2, 4, 5 and 6, columns at right). This data indicates that lack of the XBP-1 transcription factor leads to a defect in Th2 cytokine production that can be overcome by exogenous factors that skew T cell development along the Th2 pathway.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of identifying a compound that stimulates hepatocyte growth comprising:
   a) contacting hepatocytes from an XBP-1 knockout (XBP-1$^{-/-}$) mouse embryo, with a test compound; and
   b) determining the effect of the test compound on the growth of the hepatocytes, the test compound being identified as a stimulator of hepatocyte growth based on the ability of the test compound to stimulate the growth of the hepatocytes from the mouse embryo.

2. A method of identifying a compound that stimulates plasma cell differentiation comprising:
   a) contacting B cells from a chimeric XBP-1 knockout (XBP-1$^{-/-}$)/RAG-2 knockout (RAG-2$^{-/-}$) mouse, with a test compound; and
   b) determining the effect of the test compound on the differentiation of the B cells into plasma cells, the test compound being identified as a stimulator of plasma cell differentiation based on the ability of the test compound to stimulate the differentiation of the B cells from the chimeric mouse.

3. A method of identifying a compound that stimulates Th2 cell subset activity comprising:
   a) contacting T cells from a chimeric XBP-1 knockout (XBP-1$^{-/-}$)/RAG-2 knockout (RAG-2$^{-/-}$) mouse, with a test compound; and
   b) determining the effect of the test compound on Th2 cytokine production by the T cells, the test compound being identified as a stimulator of Th2 cell subset activity based on the ability of the test compound to stimulate Th2 cytokine production by the T cells from the chimeric mouse.

4. The method of any one of claims 1, 2, and 3, wherein the cells are contacted with the test compound by administering the test compound to the mouse or embryo.

5. The method of any one of claims 1, 2, and 3, wherein the cells are isolated from the mouse or embryo, and the cells are contacted with the test compound by culturing the test compound with the isolated cells.

6. The method of claim 1, wherein hepatocyte growth is determined by determining the transcription of immediate early genes.

7. The method of claim 1, wherein hepatocyte growth is determined by monitoring the incorporation of BrdU.

8. The method of claim 1, wherein hepatocyte growth is determined by TUNEL staining.

9. The method of claim 2, wherein the differentiation of the B cells into plasma cells is determined by determining immunoglobulin secretion.

10. The method of claim 2, wherein the differentiation of the B cells into plasma cells is determined by determining Syndecan-1 transcription.

11. The method of claim 3, wherein Th2 cell subset activity is determined by determining T cell cytokine production.

12. The method of claim 11, wherein the T cell cytokine is selected from the group consisting of: IL-4, IL-5, IL-6, and IL-10.

* * * * *